(12) United States Patent
Errico et al.

(10) Patent No.: US 9,821,164 B2
(45) Date of Patent: Nov. 21, 2017

(54) ELECTRICAL TREATMENT OF BRONCHIAL CONSTRICTION

(71) Applicant: ElectroCore, LLC, Basking Ridge, NJ (US)

(72) Inventors: Joseph P. Errico, Warren, NJ (US); Steven Mendez, Chester, NJ (US); Bruce J. Simon, Mountain Lakes, NJ (US); James R. Pastena, Succasunna, NJ (US); Hecheng Hu, Cedar Grove, NJ (US); Arthur Ross, Mendham, NJ (US)

(73) Assignee: Electrocore, LLC, Basking Ridge, NJ (US)

( * ) Notice: Subject to any disclaimer, the term of this patent is extended or adjusted under 35 U.S.C. 154(b) by 0 days.

(21) Appl. No.: 14/448,357

(22) Filed: Jul. 31, 2014

(65) Prior Publication Data
US 2014/0343565 A1 Nov. 20, 2014

Related U.S. Application Data

(63) Continuation of application No. 12/408,131, filed on Mar. 20, 2009, now Pat. No. 8,812,112, which is a continuation-in-part of application No. 11/591,340, filed on Nov. 1, 2006, now Pat. No. 7,747,324.

(60) Provisional application No. 60/814,313, filed on Jun. 16, 2006, provisional application No. 60/786,564, filed on Mar. 28, 2006, provisional application No.
(Continued)

(51) Int. Cl.
*A61N 1/05* (2006.01)
*A61N 1/36* (2006.01)

(52) U.S. Cl.
CPC .......... *A61N 1/3611* (2013.01); *A61N 1/0519* (2013.01); *A61N 1/3601* (2013.01); *A61N 1/36017* (2013.01); *A61N 1/36053* (2013.01); *A61N 1/36146* (2013.01);
(Continued)

(58) Field of Classification Search
CPC .............. A61N 1/3605; A61N 1/36053; A61N 1/36057; A61N 1/36114; A61N 1/362
See application file for complete search history.

(56) References Cited

U.S. PATENT DOCUMENTS

| 3,590,810 A | 7/1971 | Kopecky |
| 4,196,737 A | 4/1980 | Bevilacqua |

(Continued)

FOREIGN PATENT DOCUMENTS

| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Christopher D Koharski
*Assistant Examiner* — Natasha Patel
(74) *Attorney, Agent, or Firm* — Dentons US LLP

(57) ABSTRACT

Devices, systems and methods for treating bronchial constriction related to asthma, anaphylaxis or chronic obstructive pulmonary disease wherein the treatment includes stimulating selected nerve fibers responsible for smooth muscle dilation at a selected region within a patient's neck, thereby reducing the magnitude of constriction of bronchial smooth muscle.

15 Claims, 17 Drawing Sheets

Related U.S. Application Data

60/772,361, filed on Feb. 10, 2006, provisional application No. 60/736,002, filed on Nov. 10, 2005, provisional application No. 60/736,001, filed on Nov. 10, 2005.

(52) U.S. Cl.
CPC .......... *A61N 1/0517* (2013.01); *A61N 1/0526* (2013.01); *A61N 1/0551* (2013.01)

(56) References Cited

U.S. PATENT DOCUMENTS

| | | | |
|---|---|---|---|
| 5,458,141 | A | 10/1995 | Neil |
| 5,899,922 | A | 5/1999 | Loos |
| 5,913,876 | A * | 6/1999 | Taylor .................. A61B 17/122 128/898 |
| 5,983,131 | A | 11/1999 | Weaver et al. |
| 6,341,236 | B1 | 1/2002 | Osorio et al. |
| 6,463,327 | B1 | 10/2002 | Lurie et al. |
| 6,587,719 | B1 | 7/2003 | Barrett et al. |
| 6,610,713 | B2 | 8/2003 | Tracey |
| 7,797,041 | B2 | 9/2010 | Libbus et al. |
| 2002/0099417 | A1 | 7/2002 | Naritoku et al. |
| 2002/0183237 | A1 | 12/2002 | Puskas |
| 2003/0074039 | A1* | 4/2003 | Puskas ........................ 607/118 |
| 2004/0243182 | A1 | 12/2004 | Cohen et al. |
| 2004/0249416 | A1 | 12/2004 | Yun et al. |
| 2005/0021092 | A1 | 1/2005 | Yun et al. |
| 2005/0065574 | A1 | 3/2005 | Rezai |
| 2005/0137644 | A1 | 6/2005 | Boveja et al. |
| 2005/0143786 | A1* | 6/2005 | Boveja ............................. 607/45 |
| 2005/0197675 | A1* | 9/2005 | David .................... A61B 5/412 607/9 |
| 2006/0041277 | A1* | 2/2006 | Deem et al. ...................... 607/3 |
| 2006/0074284 | A1 | 4/2006 | Juola et al. |
| 2006/0100668 | A1 | 5/2006 | Ben-David et al. |
| 2006/0100671 | A1 | 5/2006 | Ridder |
| 2006/0173510 | A1 | 8/2006 | Besio et al. |
| 2006/0178703 | A1 | 8/2006 | Huston et al. |
| 2007/0027496 | A1* | 2/2007 | Parnis et al. .................... 607/42 |
| 2007/0123952 | A1 | 5/2007 | Strother et al. |
| 2007/0142886 | A1 | 6/2007 | Fischell et al. |
| 2007/0150006 | A1 | 6/2007 | Libbus et al. |
| 2007/0276449 | A1 | 11/2007 | Gunter et al. |
| 2008/0021512 | A1 | 1/2008 | Knudson et al. |
| 2008/0027513 | A1 | 1/2008 | Carbunaru |
| 2008/0045776 | A1 | 2/2008 | Fischell et al. |
| 2008/0132964 | A1 | 6/2008 | Cohen et al. |
| 2008/0177190 | A1 | 7/2008 | Libbus et al. |
| 2008/0208266 | A1 | 8/2008 | Lesser et al. |
| 2008/0306325 | A1 | 12/2008 | Burnett et al. |
| 2009/0157149 | A1 | 6/2009 | Wahlgren et al. |
| 2009/0234419 | A1 | 9/2009 | Maschino et al. |
| 2009/0287035 | A1 | 11/2009 | Dietrich et al. |
| 2010/0286553 | A1 | 11/2010 | Feler et al. |
| 2011/0046432 | A1 | 2/2011 | Simon et al. |
| 2011/0152967 | A1 | 6/2011 | Simon et al. |
| 2011/0213295 | A1 | 9/2011 | Henley et al. |
| 2011/0224749 | A1 | 9/2011 | Ben-David et al. |
| 2011/0230701 | A1 | 9/2011 | Simon et al. |
| 2012/0029601 | A1 | 2/2012 | Simon et al. |
| 2012/0283697 | A1 | 11/2012 | Kim et al. |
| 2012/0303080 | A1 | 11/2012 | Ben-David et al. |
| 2013/0053926 | A1* | 2/2013 | Hincapie Ordonez .............. A61B 5/4035 607/62 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

FIG. 1
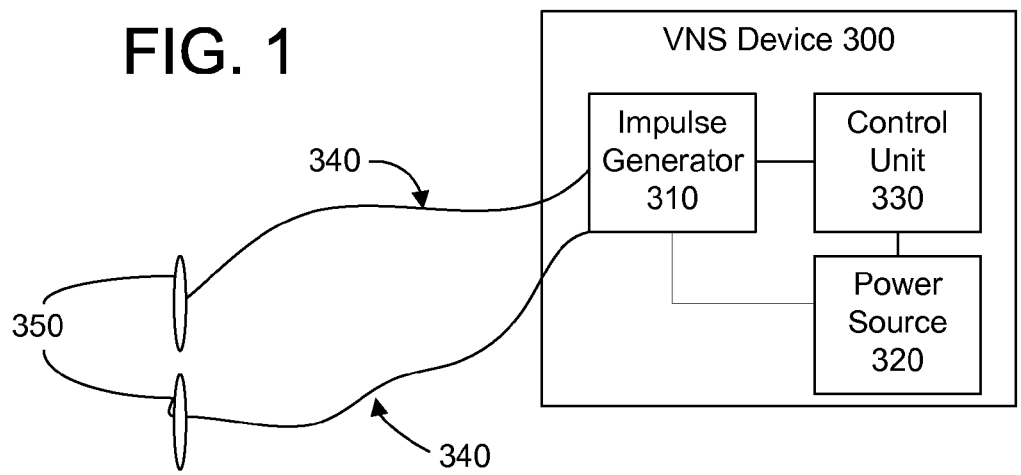
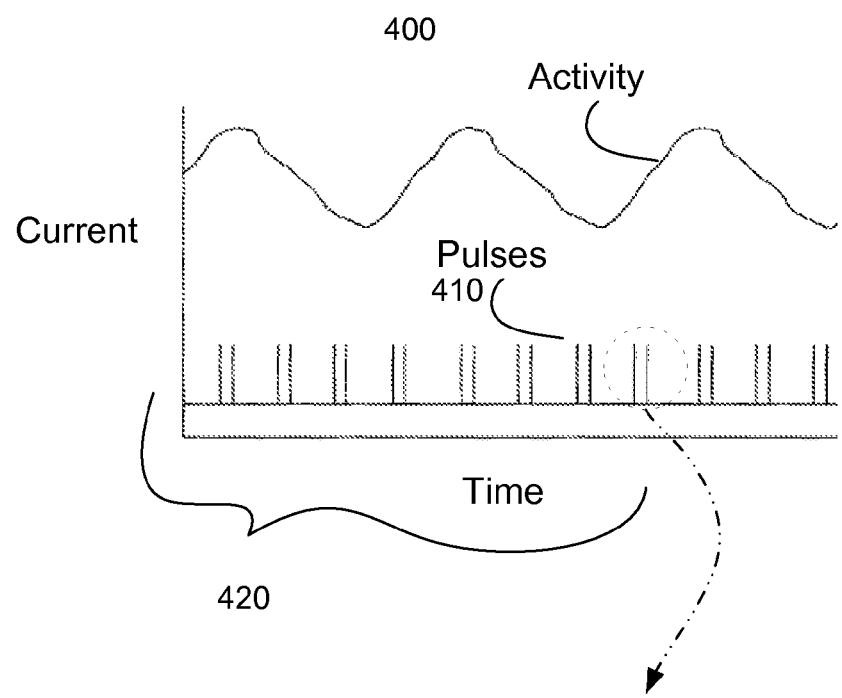
FIG. 2
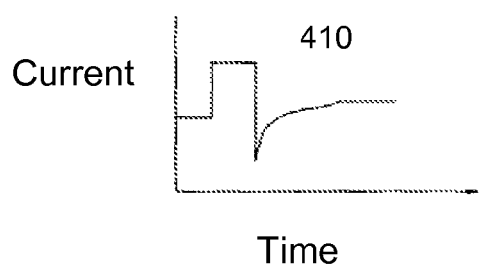

FIG. 18

| Patient ID | Initial FEV₁ % Predicted | Historical FEV₁ % Predicted | Peak % Increase FEV₁ from initial | Elapsed Time (min) to Peak FEV₁ increase | Elapsed Time until 12% FEV₁ increase |
|---|---|---|---|---|---|
| 03-001 | 61 | | 43.9 | 75 | 15 |
| 01-001 | 51 | | 41.2 | 150 | 30 |
| 04-001* | 16 | | 131.3 | 150 | 15 |
| 01-002 | 66 | | 19.7 | 90 | 90 |
| 04-002** | 52 | | 19.2 | 15 | 15 |
| Average | 49.2 | | 51.1 | 96.0 | 33.0 |

Date minus patient 04-001 and 04-002

| Patient ID | Initial FEV1 % Predicted | Historical FEV1 % Predicted | Peak % Increase FEV1 from initial | Elapsed Time (min) to Peak FEV1 increase | Elapsed Time until 12% FEV1 increase |
|---|---|---|---|---|---|
| 03-001 | 61 | | 43.9 | 75 | 15 |
| 01-001 | 51 | | 41.2 | 150 | 30 |
| 01-002 | 66 | | 19.7 | 90 | 90 |
| Average | 50.3 | | 34.9 | 105.0 | 45.0 | ously
ELECTRICAL TREATMENT OF BRONCHIAL CONSTRICTION

CROSS REFERENCE TO RELATED APPLICATIONS

The present application is a Continuation of U.S. patent application Ser. No. 12/408,131 filed 20 Mar. 2009; which is a Continuation in Part of U.S. patent application Ser. No. 11/591,340 filed 1 Nov. 2006, now U.S. Pat. No. 7,747,324 issued 29 Jun. 2010; which claims the benefit of U.S. Provisional Patent Application Nos. 60/814,313 filed 16 Jun. 2006, 60/786,564 filed 28 Mar. 2006, 60/772,361 filed 10 Feb. 2006, 60/736,002 filed 10 Nov. 2005, and 60/736,001 filed 10 Nov. 2005; each of which is incorporated herein by reference in its entirety.

BACKGROUND OF THE INVENTION

The present invention relates to the field of delivery of electrical impulses (and/or fields) to bodily tissues for therapeutic purposes, and more specifically to devices and methods for treating conditions associated with bronchial constriction There are a number of treatments for various infirmities that require the destruction of otherwise healthy tissue in order to affect a beneficial effect. Malfunctioning tissue is identified, and then lesioned or otherwise compromised in order to affect a beneficial outcome, rather than attempting to repair the tissue to its normal functionality. While there are a variety of different techniques and mechanisms that have been designed to focus lesioning directly onto the target nerve tissue, collateral damage is inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant, for example, at least one popular diet pill of the late 1990's was subsequently found to cause heart attacks and strokes.

Unfortunately, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Electrical stimulation of the brain with implanted electrodes has been approved for use in the treatment of various conditions, including pain and movement disorders including essential tremor and Parkinson's disease. The principle behind these approaches involves disruption and modulation of hyperactive neuronal circuit transmission at specific sites in the brain. As compared with the very dangerous lesioning procedures in which the portions of the brain that are behaving pathologically are physically destroyed, electrical stimulation is achieved by implanting electrodes at these sites to, first sense aberrant electrical signals and then to send electrical pulses to locally disrupt the pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into the brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neurovasculature.

One of the most successful modern applications of this basic understanding of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Around this time, it was also found that the electrical leads could be connected to the heart through veins, which eliminated the need to open the chest cavity and attach the lead to the heart wall. In 1975, the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to Deno, et al., the disclosure of which is incorporated herein by reference).

Another application of electrical stimulation of nerves has been the treatment of radiating pain in the lower extremities by means of stimulation of the sacral nerve roots at the bottom of the spinal cord (see U.S. Pat. No. 6,871,099 to Whitehurst, et al., the disclosure of which is incorporated herein by reference).

The smooth muscles that line the bronchial passages are controlled by a confluence of vagus and sympathetic nerve fiber plexuses. Spasms of the bronchi during asthma attacks and anaphylactic shock can often be directly related to pathological signaling within these plexuses. Anaphylactic shock and asthma are major health concerns.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath.

Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release of the molecules that mediate the inflammatory process. The second strategy is to provide a smooth muscle relaxant (e.g. an anti-cholinergic) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Anaphylaxis likely ranks among the other airway occluding disorders of this type as the most deadly, claiming many deaths in the United States every year. Anaphylaxis (the most severe form of which is anaphylactic shock) is a severe and rapid systemic allergic reaction to an allergen. Minute amounts of allergens may cause a life-threatening anaphylactic reaction. Anaphylaxis may occur after ingestion, inhalation, skin contact or injection of an allergen. Anaphylactic shock usually results in death in minutes if untreated. Anaphylactic shock is a life-threatening medical emergency because of rapid constriction of the airway. Brain damage sets in quickly without oxygen.

The triggers for these fatal reactions range from foods (nuts and shellfish), to insect stings (bees), to medication (radio contrasts and antibiotics). It is estimated that 1.3 to 13 million people in the United States are allergic to venom associated with insect bites; 27 million are allergic to antibiotics; and 5-8 million suffer food allergies. All of these individuals are at risk of anaphylactic shock from exposure to any of the foregoing allergens. In addition, anaphylactic shock can be brought on by exercise. Yet all are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

Anaphylactic shock requires advanced medical care immediately. Current emergency measures include rescue breathing; administration of epinephrine; and/or intubation if possible. Rescue breathing may be hindered by the closing airway but can help if the victim stops breathing on his own. Clinical treatment typically consists of antihistamines (which inhibit the effects of histamine at histamine receptors) which are usually not sufficient in anaphylaxis, and high doses of intravenous corticosteroids. Hypotension is treated with intravenous fluids and sometimes vasoconstrictor drugs. For bronchospasm, bronchodilator drugs such as salbutamol are employed.

Given the common mediators of both asthmatic and anaphylactic bronchoconstriction, it is not surprising that asthma sufferers are at a particular risk for anaphylaxis. Still, estimates place the numbers of people who are susceptible to such responses at more than 40 million in the United States alone.

Tragically, many of these patients are fully aware of the severity of their condition, and die while struggling in vain to manage the attack medically. Many of these incidents occur in hospitals or in ambulances, in the presence of highly trained medical personnel who are powerless to break the cycle of inflammation and bronchoconstriction (and life-threatening hypotension in the case of anaphylaxis) affecting their patient.

Unfortunately, prompt medical attention for anaphylactic shock and asthma are not always available. For example, epinephrine is not always available for immediate injection. Even in cases where medication and attention is available, life saving measures are often frustrated because of the nature of the symptoms. Constriction of the airways frustrates resuscitation efforts, and intubation may be impossible because of swelling of tissues.

Typically, the severity and rapid onset of anaphylactic reactions does not render the pathology amenable to chronic treatment, but requires more immediately acting medications. Among the most popular medications for treating anaphylaxis is epinephrine, commonly marketed in so-called "Epi-pen" formulations and administering devices, which potential sufferers carry with them at all times. In addition to serving as an extreme bronchodilator, epinephrine raises the patient's heart rate dramatically in order to offset the hypotension that accompanies many reactions. This cardiovascular stress can result in tachycardia, heart attacks and strokes.

Chronic obstructive pulmonary disease (COPD) is a major cause of disability, and is the fourth leading cause of death in the United States. More than 12 million people are currently diagnosed with COPD. An additional 12 million likely have the disease and don't even know it. COPD is a progressive disease that makes it hard for the patient to breathe. COPD can cause coughing that produces large amounts of mucus, wheezing, shortness of breath, chest tightness and other symptoms. Cigarette smoking is the leading cause of COPD, although long-term exposure to other lung irritants, such as air pollution, chemical fumes or dust may also contribute to COPD. In COPD, less air flows in and out of the bronchial airways for a variety of reasons, including loss of elasticity in the airways and/or air sacs, inflammation and/or destruction of the walls between many of the air sacs and overproduction of mucus within the airways.

The term COPD includes two primary conditions: emphysema and chronic obstructive bronchitis. In emphysema, the walls between many of the air sacs are damaged, causing them to lose their shape and become floppy. This damage also can destroy the walls of the air sacs, leading to fewer and larger air sacs instead of many tiny ones. In chronic obstructive bronchitis, the patient suffers from permanently irritated and inflamed bronchial tissue that is slowly and progressively dying. This causes the lining to thicken and form thick mucus, making it hard to breathe. Many of these patients also experience periodic episodes of acute airway reactivity (i.e., acute exacerbations), wherein the smooth muscle surrounding the airways goes into spasm, resulting in further constriction and inflammation of the airways. Acute exacerbations occur, on average, between two and three times a year in patients with moderate to severe COPD and are the most common cause of hospitalization in these patients (mortality rates are estimated about 11%. Frequent acute exacerbations of COPD cause lung function to deteriorate quickly, and patients never recover to the condition they were in before the last exacerbation. Similar to asthma, current medical management of these acute exacerbations is often insufficient.

Unlike cardiac arrhythmias, which can be treated chronically with pacemaker technology, or in emergent situations with equipment like defibrillators (implantable and external), there is virtually no commercially available medical equipment that can chronically reduce the baseline sensitivity of the muscle tissue in the airways to reduce the predisposition to asthma attacks, reduce the symptoms of COPD or to break the cycle of bronchial constriction associated with an acute asthma attack or anaphylaxis.

Accordingly, there is a need in the art for new products and methods for treating the immediate symptoms of bronchial constriction resulting from pathologies such as anaphylactic shock, asthma and COPD.

SUMMARY OF THE INVENTION

The present invention involves products and methods of treatment of asthma, COPD, anaphylaxis, and other pathologies involving the constriction of the primary airways, utilizing an electrical signal that may be applied directly to, or in close proximity to, a selected nerve to temporarily stimulate, block and/or modulate the signals in the selected nerve. The present invention is particularly useful for the acute relief of symptoms associated with bronchial constriction, i.e., asthma attacks, COPD exacerbations and/or anaphylactic reactions. The teachings of the present invention provide an emergency response to such acute symptoms, by producing immediate airway dilation and/or heart function increase to enable subsequent adjunctive measures (such as the administration of epinephrine) to be effectively employed.

In one aspect of the present invention, a method of treating bronchial constriction comprises stimulating selected nerve fibers responsible for reducing the magnitude of constriction of smooth bronchial muscle to increase the activity of the selected nerve fibers. In a preferred embodiment, the selected nerve fibers are inhibitory nonadrenergic noncholinergic nerve fibers (iNANC) which are generally responsible for bronchodilation. Stimulation of these iNANC fibers increases their activity, thereby increasing bronchodilation and facilitating opening of the airways of the mammal. The stimulation may occur through direct stimulation of the efferent iNANC fibers that produce bronchodilation or indirectly through stimulation of the afferent sympathetic or parasympathetic nerves which carry signals to the brain and then back down through the iNANC nerve fibers to the bronchial passages.

In one embodiment, the iNANC nerve fibers are associated with the vagus nerve and are thus directly responsible for bronchodilation. In an alternative embodiment, the iNANC fibers are interneurons that are completely contained within the walls of the bronchial airways. These interneurons are responsible for modulating the cholinergic nerves in the bronchial passages. In this embodiment, the increased activity of the iNANC interneurons will cause inhibition or blocking of the cholinergic nerves responsible for bronchial constriction, thereby facilitating opening of the airways.

The stimulating step is preferably carried out without substantially stimulating excitatory nerve fibers, such as parasympathetic cholinergic nerve fibers, that are responsible for increasing the magnitude of constriction of smooth muscle. In this manner, the activity of the iNANC nerve fibers are increased without increasing the activity of the cholinergic fibers which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking/inhibiting signal may be separately applied to the inhibitory nerves; or it may be part of the same signal that is applied to the iNANC nerve fibers.

In an alternative embodiment, a method of treating bronchial constriction comprises stimulating, inhibiting, blocking or otherwise modulating selected efferent sympathetic nerves responsible for mediating bronchial passages either directly or indirectly. The selected efferent sympathetic nerves may be nerves that directly innervate the bronchial smooth muscles. It has been postulated that asthma patients typically have more sympathetic nerves that directly innervate the bronchial smooth muscle than individuals that do not suffer from asthma. In yet other embodiments, the method includes stimulating, inhibiting, blocking or otherwise modulating nerves that release systemic bronchodilators or nerves that directly modulate parasympathetic ganglia transmission (by stimulation or inhibition of preganglionic to postganglionic transmissions).

In another aspect of the invention, a method of treating bronchial constriction includes applying an electrical impulse to a target region in the patient and acutely reducing the magnitude of bronchial constriction in the patient. As used herein, the term acutely means that the electrical impulse immediately begins to interact with one or more nerves to produce a response in the patient. The electrical impulse is preferably sufficient to increase the Forced Expiratory Volume in about 1 second ($FEV_1$) of the patient by a clinically significant amount in a period of time less than about 6 hours, preferably less than about 3 hours and more preferably less than about 90 minutes. A clinically significant amount is defined herein as at least an about 12% increase in the patient's $FEV_1$ versus the FEV1 measured prior to application of the electrical impulse. In an exemplary embodiment, the electrical impulse is sufficient to increase the FEV1 by at least about 19% over the $FEV_1$ as predicted.

In another aspect of the invention, a method for treating bronchial constriction comprises applying one or more electrical impulse(s) of a frequency from about 15 Hz to about 50 Hz to a selected region within a patient to reduce a magnitude of constriction of bronchial smooth muscle. In a preferred embodiment, the method includes introducing one or more electrodes to a target region in a patient's neck and applying an electrical impulse to the target region to stimulate, inhibit or otherwise modulate selected nerve fibers that interact with bronchial smooth muscle. Preferably, the target region is adjacent to, or in close proximity with, the carotid sheath.

Applicant has made the unexpected discovered that applying an electrical impulse to a selected region of a patient's neck within this particular frequency range results in almost immediate and significant improvement in bronchodilation, as discussed in further detail below. Applicant has further discovered that applying electrical impulses outside of the selected frequency range (from about 15 Hz to about 50 Hz) does not result in significant improvement and, in some cases, may worsen the patient's bronchoconstriction. Preferably, the frequency is about 25 Hz. In this embodiment, the electrical impulse(s) are of an amplitude from about 0.5 to about 12 volts and have a pulsed on-time from about 50 to 500 microseconds, preferably from about 200 microseconds to about 400 microseconds. The preferred voltage will depend on the size and shape of the electrodes and the distance between the electrode(s) and the target nerves. In certain embodiments wherein the electrical impulse is applied through a percutaneous lead, or from within the patient's esophagus or trachea, the electrical impulse preferably has an amplitude of at least about 6 volts and more preferably from about 7 volts to about 12 volts. In other embodiments wherein the electrical impulse is applied directly to a nerve (e.g., via a nerve cuff), the amplitude is preferably lower, i.e., less than about 6 volts and more preferably from about 0.1 volts to about 2 volts.

The electrical impulse(s) are applied in a manner that reduces the constriction of the smooth muscle lining the bronchial passages to relieve the spasms that occur during anaphylactic shock, acute exacerbations of COPD or asthma attacks. In some embodiments, the mechanisms by which the appropriate impulse is applied to the selected region within the patient include positioning the distal ends of an electrical lead or leads in the vicinity of the nervous tissue controlling the pulmonary and/or cardiac muscles, which leads are coupled to an implantable or external electrical impulse generating device. The electric field generated at the distal tip of the lead creates a field of effect that permeates the target nerve fibers and causes the stimulating, blocking and/or modulation of signals to the subject muscles, and/or the blocking and/or affecting of histamine response. It shall also be understood that leadless impulses as shown in the art may also be utilized for applying impulses to the target regions.

The electrical leads may be positioned at the target site within the patient through a variety of different methods. In one embodiment, an introducer comprising an electrode is passed percutaneously through the patient's neck to a region adjacent to or in close proximity to the carotid sheath. In an alternative embodiment, the introducer is advanced through the patient's esophagus to a position adjacent to or in close proximity to the vagus nerve. In this embodiment, the introducer may be, for example, a nasogastral (NG) tube having an internal passageway and at least one electrode coupled to the external surface of the NG tube. In yet another embodiment, the introducer is advanced through the patient's tracheal, e.g. via an endotracheal tube. In yet another embodiment, an electrode is implanted in the patient adjacent to or around the vagus nerve and activated by a remote control mechanism outside of the patient. In this embodiment, activation of such impulses via the remote control may be directed by a health care provider or manually by a patient suffering from bronchospasm.

The novel systems, devices and methods for treating bronchial constriction are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 is a schematic view of a nerve modulating device according to the present invention;

FIG. 2 illustrates an exemplary electrical voltage/current profile for a blocking and/or modulating impulse applied to a portion or portions of a nerve in accordance with an embodiment of the present invention;

FIGS. 15-18 graphically illustrate exemplary experimental data obtained on human patients in accordance with multiple embodiments of the present invention;

DETAILED DESCRIPTION OF THE PREFERRED EMBODIMENTS

Figure 3:
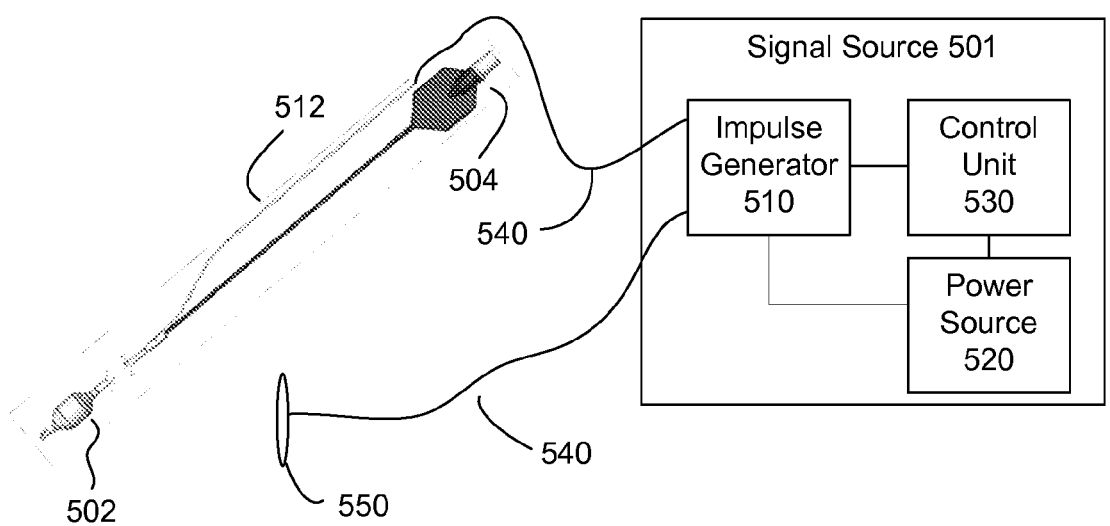
FIG. 3 is a schematic view of a nerve modulating device for introduction through a patient's esophagus according to one embodiment of the prevent invention.

In the present invention, electrical energy is applied to one or more electrodes to deliver an electromagnetic field to a patient. The techniques of the present invention may be performed in a conventional open surgery environment or in a minimally invasive manner through a natural body orifice (e.g., esophagus or trachea), percutaneously through the patient's skin or using cannulas or port access devices. The invention is particularly useful for applying electrical impulses that interact with the signals of one or more nerves, or muscles, to achieve a therapeutic result, such as relaxation of the smooth muscle of the bronchia. In particular, the present invention provides methods and devices for immediate relief of acute symptoms associated with bronchial constriction such as asthma attacks, COPD exacerbations and/or anaphylactic reactions.

For convenience, the remaining disclosure will be directed specifically to the treatment in or around the carotid sheath with devices introduced through a percutaneous penetration in a patient's neck or through the esophagus or through the trachea of a patient, but it will be appreciated that the systems and methods of the present invention can be applied equally well to other tissues and nerves of the body, including but not limited to other parasympathetic nerves, sympathetic nerves, spinal or cranial nerves. In addition, the present invention can be used to directly or indirectly stimulate or otherwise modulate nerves that innervate bronchial smooth muscle.

While the exact physiological causes of asthma, COPD and anaphylaxis have not been determined, the present invention postulates that the direct mediation of the smooth muscles of the bronchia is the result of activity in one or more nerves near or in the carotid sheath. In the case of asthma, it appears that the airway tissue has both (i) a hypersensitivity to the allergen that causes the overproduction of the cytokines that stimulate the cholinergic receptors of the nerves and/or (ii) a baseline high parasympathetic tone or a high ramp up to a strong parasympathetic tone when confronted with any level of cholenergic cytokine. The combination can be lethal. Anaphylaxis appears to be mediated predominantly by the hypersensitivity to an allergen causing the massive overproduction of cholenergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. Experience has shown that severing the vagus nerve (an extreme version of reducing the parasympathetic tone) has an effect similar to that of epinephrine on heart rate and bronchial diameter in that the heart begins to race (tachycardia) and the bronchial passageways dilate.

In accordance with the present invention, the delivery, in a patient suffering from severe asthma, COPD or anaphylactic shock, of an electrical impulse sufficient to stimulate, block and/or modulate transmission of signals will result in relaxation of the bronchi smooth muscle, dilating airways and/or counteract the effect of histamine on the vagus nerve. Depending on the placement of the impulse, the stimulating, blocking and/or modulating signal can also raise the heart function.

Stimulating, blocking and/or modulating the signal in selected nerves to reduce parasympathetic tone provides an immediate emergency response, much like a defibrillator, in situations of severe asthma or COPD attacks or anaphylactic shock, providing immediate temporary dilation of the airways and optionally an increase of heart function until subsequent measures, such as administration of epinephrine, rescue breathing and intubation can be employed. Moreover, the teachings of the present invention permit immediate airway dilation and/or heart function increase to enable subsequent life saving measures that otherwise would be ineffective or impossible due to severe constriction or other physiological effects. Treatment in accordance with the present invention provides bronchodilation and optionally increased heart function for a long enough period of time so that administered medication such as epinephrine has time to take effect before the patient suffocates.

In a preferred embodiment, a method of treating bronchial constriction comprises stimulating selected nerve fibers responsible for reducing the magnitude of constriction of smooth bronchial muscle to increase the activity of the selected nerve fibers. Certain signals of the parasympathetic nerve fibers cause a constriction of the smooth muscle surrounding the bronchial passages, while other signals of the parasympathetic nerve fibers carry the opposing signals that tend to open the bronchial passages. Specifically, it should be recognized that certain signals, such as cholinergic fibers mediate a response similar to that of histamine, while other signals (e.g., nonadrenergic, noncholinergic or iNANC nerve fibers) generate an effect similar to epinephrine. Given the postulated balance between these signals, stimulating the iNANC nerve fibers and/or blocking or removing the cholinergic signals should create an imbalance emphasizing bronchodilation.

In one embodiment of the present invention, the selected nerve fibers are inhibitory nonadrenergic noncholinergic (iNANC) nerve fibers which are generally responsible for bronchodilation. Stimulation of these iNANC fibers increases their activity, thereby increasing bronchodilation and facilitating opening of the airways of the mammal. The stimulation may occur through direct stimulation of the efferent iNANC fibers that cause bronchodilation or indirectly through stimulation of the afferent sympathetic or parasympathetic nerves which carry signals to the brain and then back down through the iNANC nerve fibers to the bronchial passages.

In certain embodiments, the iNANC nerve fibers are associated with the vagus nerve and are thus directly responsible for bronchodilation. Alternatively, the iNANC fibers may be interneurons that are completely contained within the walls of the bronchial airways. These interneurons are responsible for modulating the cholinergic nerves in the bronchial passages. In this embodiment, the increased activity of the iNANC interneurons will cause inhibition or blocking of the cholinergic nerves responsible for bronchial constriction, thereby facilitating opening of the airways.

As discussed above, certain parasympathetic signals mediate a response similar to histamine, thereby causing a constriction of the smooth muscle surrounding the bronchial passages. Accordingly, the stimulating step of the present invention is preferably carried out without substantially stimulating the parasympathetic nerve fibers, such as the cholinergic nerve fibers associated with the vagus nerve, that are responsible for increasing the magnitude of constriction of smooth muscle. In this manner, the activity of the iNANC nerve fibers are increased without increasing the activity of the adrenergic fibers which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking signal may be separately applied to the inhibitory nerves; or it may be part of the same signal that is applied to the iNANC nerve fibers.

While it is believed that there are little to no direct sympathetic innervations of the bronchial smooth muscle in most individuals, recent evidence has suggested asthma patients do have such sympathetic innervations within the bronchial smooth muscle. In addition, the sympathetic nerves may have an indirect effect on the bronchial smooth muscle. Accordingly, alternative embodiments of the prevent invention contemplate a method of stimulating selected efferent sympathetic nerves responsible for mediating bronchial passages either directly or indirectly. The selected efferent sympathetic nerves may be nerves that directly innervate the smooth muscles, nerves that release systemic bronchodilators or nerves that directly modulate parasympathetic ganglia transmission (by stimulation or inhibition of preganglionic to postganglionic transmissions).

Method and devices of the present invention are particularly useful for providing substantially immediate relief of acute symptoms associated with bronchial constriction such as asthma attacks, COPD exacerbations and/or anaphylactic reactions. One of the key advantages of the present invention is the ability to provide almost immediate dilation of the bronchial smooth muscle in patients suffering from acute bronchoconstriction, opening the patient's airways and allowing them to breathe and more quickly recover from an acute episode (i.e., a relatively rapid onset of symptoms that are typically not prolonged or chronic).

The magnitude of bronchial constriction in a patient is typically expressed in a measurement referred to as the Forced Expiratory Volume in about 1 second ($FEV_1$). $FEV_1$ represents the amount of air a patient exhales (expressed in liters) in the first second of a pulmonary function test, which is typically performed with a spirometer. The spirometer compares the $FEV_1$ result to a standard for the patient, which is based on the predicted value for the patient's weight, height, sex, age and race. This comparison is then expressed as a percentage of the $FEV_1$ as predicted. Thus, if the volume of air exhaled by a patient in the first second is about 60% of the predicted value based on the standard, the $FEV_1$ will be expressed in both the actual liters exhaled and as a percentage of predicted (i.e., about 60% of predicted).

As will be discussed in more detail in the experiments below, applicants have disclosed a system and method for increasing a patient's $FEV_1$ in a relatively short period of time. Preferably, the electrical impulse applied to the patient is sufficient to increase the $FEV_1$ of the patient by a clinically significant amount in a period of time less than about 6 hours, preferably less than about 3 hours and more preferably less than about 90 minutes. In an exemplary embodiment, the clinically significant increase in $FEV_1$ occurs in less than about 15 minutes. A clinically significant amount is defined herein as at least an about 12% increase in the patient's $FEV_1$ versus the $FEV_1$ prior to application of the electrical impulse.

FIG. 1 is a schematic diagram of a nerve modulating device 300 for delivering electrical impulses to nerves for the treatment of bronchial constriction or hypotension associated with anaphylactic shock, COPD or asthma. As shown, device 300 may include an electrical impulse generator 310; a power source 320 coupled to the electrical impulse generator 310; a control unit 330 in communication with the electrical impulse generator 310 and coupled to the power source 320; and electrodes 340 coupled to the electrical impulse generator 310 for attachment via leads 350 to one or more selected regions of a nerve (not shown). The control unit 330 may control the electrical impulse generator 310 for generation of a signal suitable for amelioration of the bronchial constriction or hypotension when the signal is applied via the electrodes 340 to the nerve. It is noted that nerve modulating device 300 may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention.

FIG. 2 illustrates an exemplary electrical voltage/current profile for a stimulating, blocking and/or modulating impulse applied to a portion or portions of selected nerves in accordance with an embodiment of the present invention. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the stimulating, blocking and/or modulating impulse 410 to the nerve via leads 350. For percutaneous, esophageal or endotracheal use, the nerve modulating device 300 may be available to the surgeon as external emergency equipment. For subcutaneous use, device 300 may be surgically implanted, such as in a subcutaneous pocket of the abdomen. Nerve modulating device 300 may be powered and/or recharged from outside the body or may have its own power source 320. By way of example, device 300 may be purchased commercially. Nerve modulating device 300 is preferably programmed with a physician programmer, such as a Model 7432 also available from Medtronic, Inc.

The parameters of the modulation signal 400 are preferably programmable, such as the frequency, amplitude, duty cycle, pulse width, pulse shape, etc. In the case of an implanted pulse generator, programming may take place before or after implantation. For example, an implanted pulse generator may have an external device for communication of settings to the generator. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in U.S. Patent Publication No.: 2005/0216062 (the entire disclosure of which is incorporated herein by reference), may be employed. U.S. Patent Publication No.: 2005/0216062 discloses a multi-functional electrical stimulation (ES) system adapted to yield output signals for effecting, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

The electrical leads 350 and electrodes 340 are preferably selected to achieve respective impedances permitting a peak pulse voltage in the range from about 0.2 volts to about 20 volts.

The stimulating, blocking and/or modulating impulse signal 410 preferably has a frequency, an amplitude, a duty cycle, a pulse width, a pulse shape, etc. selected to influence the therapeutic result, namely stimulating, blocking and/or modulating some or all of the transmission of the selected nerve. For example the frequency may be about 1 Hz or greater, such as from about 15 Hz to about 50 Hz, more preferably around 25 Hz. The modulation signal may have a pulse width selected to influence the therapeutic result, such as about 20 µS or greater, such as from about 20 µS to about 1000 µS. The modulation signal may have a peak voltage amplitude selected to influence the therapeutic result, such as about 0.2 volts or greater, such as from about 0.2 volts to about 20 volts.

In a preferred embodiment of the invention, a method of treating bronchial constriction comprises applying one or more electrical impulse(s) of a frequency from about 15 Hz to about 50 Hz to a selected region of the vagus nerve to reduce a magnitude of constriction of bronchial smooth muscle. As discussed in more detail below, applicant has made the unexpected discovered that applying an electrical impulse to a selected region of the vagus nerve within this particular frequency range results in almost immediate and significant improvement in bronchodilation, as discussed in further detail below. Applicant has further discovered that applying electrical impulses outside of the selected frequency range (from about 15 Hz to about 50 Hz) does not result in immediate and significant improvement in bronchodilation. Preferably, the frequency is about 25 Hz. In this embodiment, the electrical impulse(s) are of an amplitude of from about 0.75 to about 12 volts (depending on the size and shape of the electrodes and the distance between the electrodes and the selected nerve(s)) and have a pulsed on-time from about 50 to about 500 microseconds, preferably about 200 microseconds to about 400 microseconds.

In accordance with one embodiment, nerve modulating device 300 is provided in the form of a percutaneous or subcutaneous implant that can be reused by an individual. In accordance with another embodiment, devices in accordance with the present invention are provided in a "pacemaker" type form, in which electrical impulses 410 are generated to a selected region of the nerve by device 300 on an intermittent basis to create in the patient a lower reactivity of the nerve to upregulation signals.

FIG. 3 illustrates an exemplary nerve modulating device 500 for use in the esophagus of a patient. As shown, device 500 includes a signal source 501 that operates to apply at least one electrical signal to an NG tube 504 (via lead 540). As discussed above, signal source 501 preferably includes an impulse generator 510, a control unit 530 and a power source 520 in communication with impulse generator 510. NG tube 504 includes an internal conductor 512 that couples lead 540 to an electrode assembly 502 at the distal portion of NG tube 504. In this embodiment, device 500 further includes a return electrode 550 coupled to impulse generator 510 via lead 540. Return electrode 550 is typically placed on an outer skin surface of the patient (not shown), as is well known in the art.

In use, electrode assembly 502 is inserted into the esophagus of a patient past a cricoid cartilage of the patient, an electromagnetic field emanates from the electrode assembly 502 to the anatomy of the patient in the vicinity of the esophagus to achieve the therapeutic result. In the exemplary embodiment, electrode assembly 502 comprises a balloon electrode device that is described in more detail in commonly assigned co-pending U.S. patent application Ser. No. 12/338,191, filed Dec. 18, 2008 now U.S. Pat. No. 8,209,034 issued Jun. 26, 2012, the complete disclosure of which is incorporated herein by reference. It will be recognized by those skilled in the art, however, that a variety of different electrode assemblies may be used with the present invention.

Figure 4:
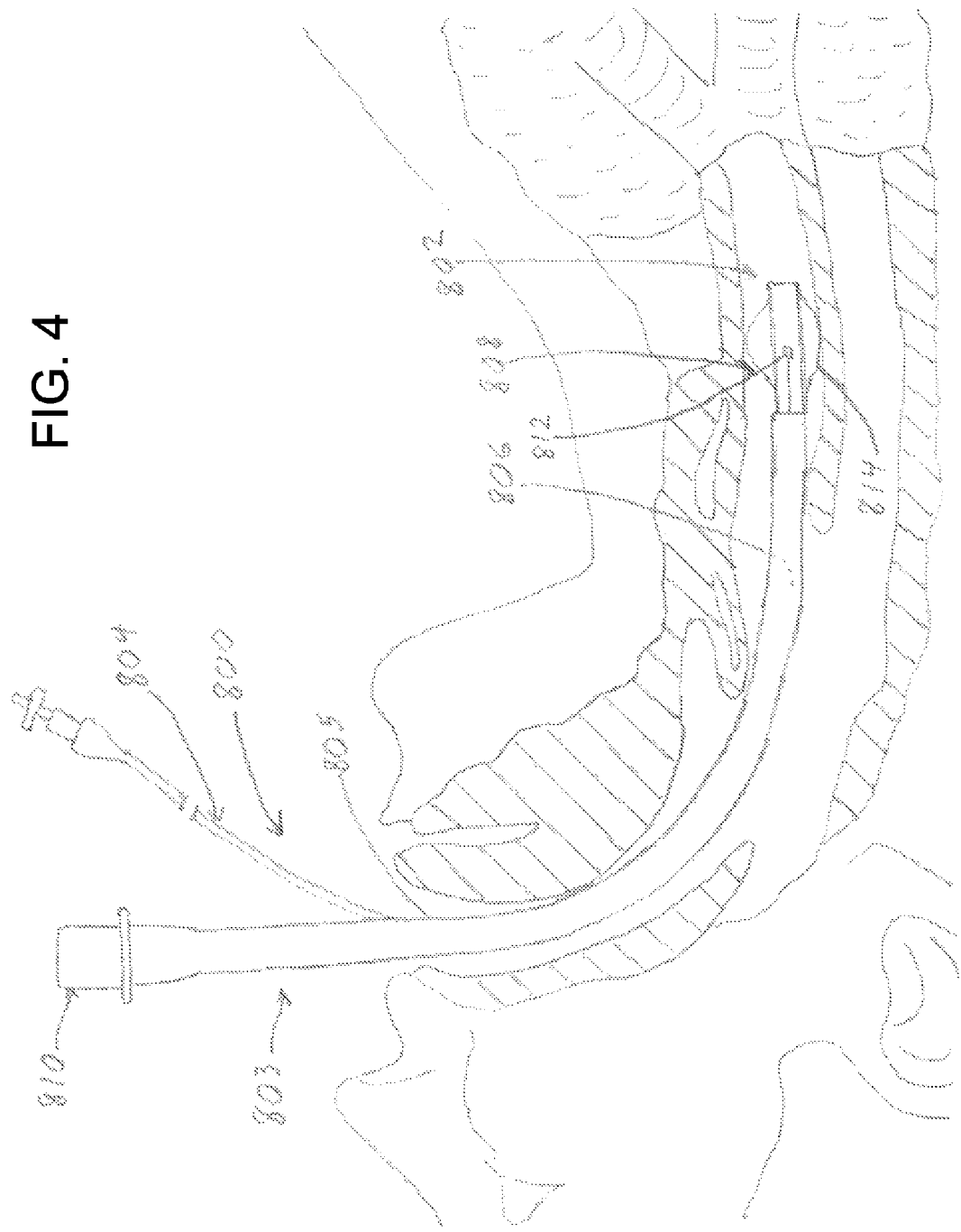
FIG. 4 illustrates an alternative embodiment of an exemplary nerve modulating device for use in a patient's trachea according to the present invention.

Referring now to FIG. 4, an alternative embodiment is illustrated for treatment of selected nerves within a patient's neck with a device 800 introduced through the trachea 802 of a patient. As shown, device 800 includes an endotracheal tube 803 that is inserted into the patient under intubation as is well known in the art. Tube 803 comprises a flexible shaft 805 with an inner lumen 806, and a distal electrode assembly 808. As in the previous embodiment, electrode assembly 502 comprises a balloon electrode device that is described in more detail in U.S. patent application Ser. No. 12/338,191, now U.S. Pat. No. 8,209,034 issued Jun. 26, 2012, but it should be understood that a variety of different electrode assemblies may be used with the present invention. Electrode assembly 808 may be an integral part of tube 803 or it may be a separate device that is inserted through the inner lumen 806 of a standard endotracheal tube. Many types of conventional endotracheal tubes may be used, such as oral un-cuffed, oral cuffed, Rae tube, nasal tube, reinforced tube, double-lumen tubes and the like. Tube 803 also includes a fluid passage 804 fluidly coupling the inner lumen 806 with a source of electrically conductive fluid (not shown) and a proximal port 810 for coupling to a source of electrical energy (also not shown). Tube 802 may also include an aspiration lumen (not shown) for aspirating the conductive fluid and/or other bodily fluids as is well known in the art.

Prior to discussing experimental results, a general approach to treating bronchial constriction in accordance with one or more embodiments of the invention may include a method of (or apparatus for) treating bronchial constriction associated with anaphylactic shock, COPD or asthma, comprising applying at least one electrical impulse to one or more selected nerve fibers of a mammal in need of relief of bronchial constriction. The method may include: introducing one or more electrodes to the selected regions near or adjacent to the selected nerve fibers, such as certain fibers near or around the carotid sheath; and applying one or more electrical stimulation signals to the electrodes to produce the at least one electrical impulse, wherein the one or more electrical stimulation signals are of a frequency from about 15 Hz to about 50 Hz.

The one or more electrical stimulation signals may be of an amplitude of from about 1 volt to about 12 volts, depending on the size and shape of the electrodes and the distance between the electrodes and the selected nerve fibers. The one or more electrical stimulation signals may be one or more of a full or partial sinusoid, square wave, rectangular wave, and/or triangle wave. The one or more electrical stimulation signals may have a pulsed on-time from about 50 to about 500 microseconds, such as about 100, 200 or 400 microseconds. The polarity of the pulses may be maintained either positive or negative. Alternatively, the polarity of the pulses may be positive for some periods of the wave and negative for some other periods of the wave. By way of example, the polarity of the pulses may be altered about every second.

In one particular embodiment of the present invention, electrical impulses are delivered to one or more portions of the vagus nerve. The vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguus and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, bronchodilation, vocalization and contraction of the facial muscles in relation to emotional states. Generally speaking, this portion of the vagus nerve regulates parasympathetic tone. The VVC inhibition is released (turned off) in states of alertness. This in turn causes cardiac vagal tone to decrease and airways to open, to support responses to environmental challenges.

The parasympathetic tone is balanced in part by sympathetic innervations, which generally speaking supplies signals tending to relax the bronchial muscles so overconstriction does not occur. Overall, airway smooth muscle tone is dependent on several factors, including parasympathetic input, inhibitory influence of circulating epinephrine, iNANC nerves and sympathetic innervations of the parasympathetic ganglia. Stimulation of certain nerve fibers of the vagus nerve (upregulation of tone), such as occurs in asthma or COPD attacks or anaphylactic shock, results in airway constriction and a decrease in heart rate. In general, the pathology of severe asthma, COPD and anaphylaxis appear to be mediated by inflammatory cytokines that overwhelm receptors on the nerve cells and cause the cells to massively upregulate the parasympathetic tone.

The methods described herein of applying an electrical impulse to a selected region of the vagus nerve may further be refined such that the at least one region may comprise at least one nerve fiber emanating from the patient's tenth cranial nerve (the vagus nerve), and in particular, at least one of the anterior bronchial branches thereof, or alternatively at least one of the posterior bronchial branches thereof. Preferably the impulse is provided to at least one of the anterior pulmonary or posterior pulmonary plexuses aligned along the exterior of the lung. As necessary, the impulse may be directed to nerves innervating only the bronchial tree and lung tissue itself. In addition, the impulse may be directed to a region of the vagus nerve to stimulate, block and/or modulate both the cardiac and bronchial branches. As recognized by those having skill in the art, this embodiment should be carefully evaluated prior to use in patients known to have preexisting cardiac issues.

Experiments were performed to identify exemplary methods of how electrical signals can be supplied to the peripheral nerve fibers that innervate and/or control the bronchial smooth muscle to (i) reduce the sensitivity of the muscle to the signals to constrict, and (ii) to blunt the intensity of, or break the constriction once it has been initiated. In particular, specific signals were applied to the selected nerves in guinea pigs to produce selective stimulation, interruption or reduction in the effects of nerve activity leading to attenuation of histamine-induced bronchoconstriction.

Male guinea pigs (400 g) were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with the nerve stimulation. In these experiments, vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, nerve stimulation was attempted at variations of frequency, voltage and pulse duration to identify parameters that attenuate responses to i.v. histamine. Bronchoconstriction in response to i.v. histamine is known to be due both to direct airway smooth muscle effects and to stimulation of vagal nerves to release acetylcholine.

At the end of vagal nerve challenges, atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP shows blood pressure, second line AP1 shows airway pressure, third line AP2 shows airway pressure on another sensor, the last line HR is the heart rate derived from the pulses in the blood pressure.

In the first animals, the signal frequency applied was varied from less than 1 Hz through 2,000 Hz, and the voltage was varied from 1V to 12V. Initial indications seemed to show that an appropriate signal was 1,000 Hz, 400 µs, and 6-10V.

Figure 5:
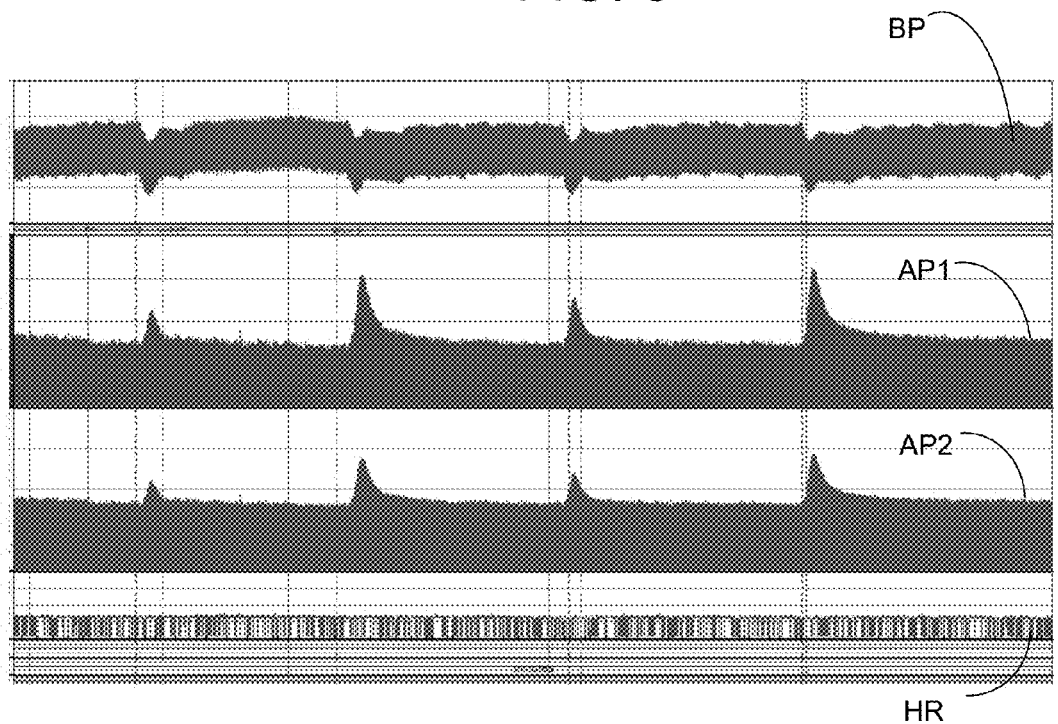
FIGS. 5-14 graphically illustrate exemplary experimental data obtained on guinea pigs in accordance with multiple embodiments of the present invention.

FIG. 5 graphically illustrates exemplary experimental data on guinea pig #2. More specifically, the graphs of FIG. 5 show the effect of a 1000 Hz, 400 µS, 6V square wave signal applied simultaneously to both left and right branches of the vagus nerve in guinea pig #2 when injected with 12 µg/kg histamine to cause airway pressure to increase. The first peak in airway pressure is histamine with the electric signal applied to the vagus, the next peak is histamine alone (signal off), the third peak is histamine and signal again, fourth peak is histamine alone again. It is clearly shown that the increase in airway pressure due to histamine is reduced in the presence of the 1000 Hz, 400 µS and 6V square wave on the vagus nerve. The animal's condition remained stable, as seen by the fact that the blood pressure and heart rate are not affected by this electrical signal.

After several attempts on the same animal to continue to reproduce this effect with the 1,000 Hz signal, however, we observed that the ability to continuously stimulate and suppress airway constriction was diminished, and then lost. It appeared that the nerve was no longer conducting. This conclusion was drawn from the facts that (i) there was some discoloration of the nerve where the electrode had been making contact, and (ii) the effect could be resuscitated by moving the lead distally to an undamaged area of the nerve, i.e. toward the organs, but not proximally, i.e., toward the brain. The same thing occurred with animal #3. It has been hypothesized that the effect seen was, therefore, accompanied by a damaging of the nerve, which would not be clinically desirable.

To resolve the issue, in the next animal (guinea pig #4), we fabricated a new set of electrodes with much wider contact area to the nerve. With this new electrode, we started investigating signals from 1 Hz to 3,000 Hz again. This time, the most robust effectiveness and reproducibility was found at a frequency of 25 Hz, 400 µs, 1V.

Figure 6:
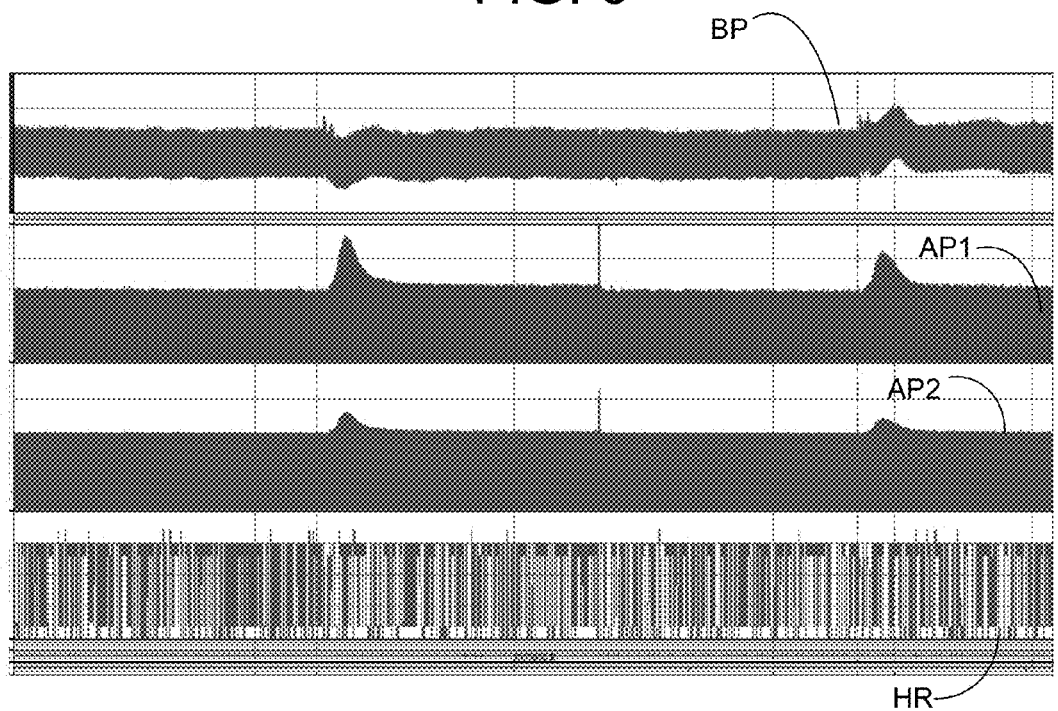

FIG. 6 graphically illustrates exemplary experimental data on guinea pig #5. The graphs of FIG. 6 show the effect of a 25 Hz, 400 μs, 1V square wave signal applied to both left and right vagus nerve in guinea pig #5 when injected with 8 μg/kg histamine to cause airway pressure to increase. The first peak in airway pressure is from histamine alone, the next peak is histamine and signal applied. It is clearly shown that the increase in airway pressure due to histamine is reduced in the presence of the Hz, 400 μS, 1V square wave on the vagus nerve.

Figure 7:
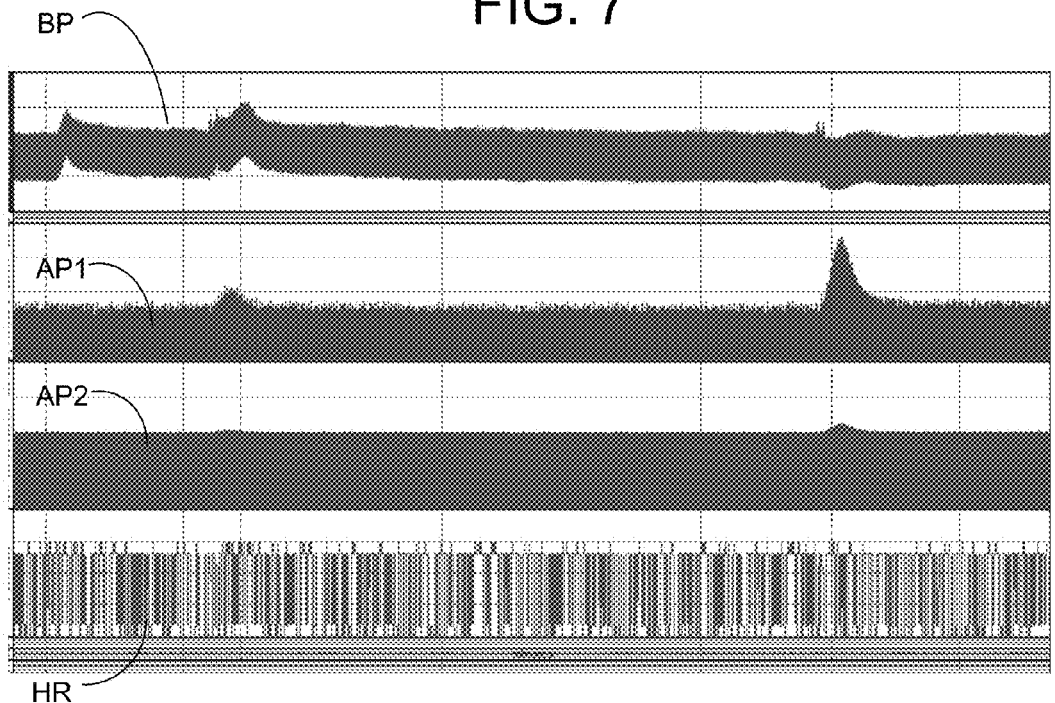

FIG. 7 graphically illustrates additional exemplary experimental data on guinea pig #5. The graphs of FIG. 7 show the effect of a 25 Hz, 200 μS, 1V square wave signal applied to both of the left and right vagus nerves in guinea pig #5 when injected with 8 μg/kg histamine to cause airway pressure to increase. The second peak in airway pressure is from histamine alone, the first peak is histamine and signal applied. It is clearly shown that the increase in airway pressure due to histamine is reduced in the presence of the 25 Hz, 200 μS, 1V square wave on the vagus nerve. It is clear that the airway pressure reduction is even better with the 200 μS pulse width than the 400 μS signal.

Figure 8:
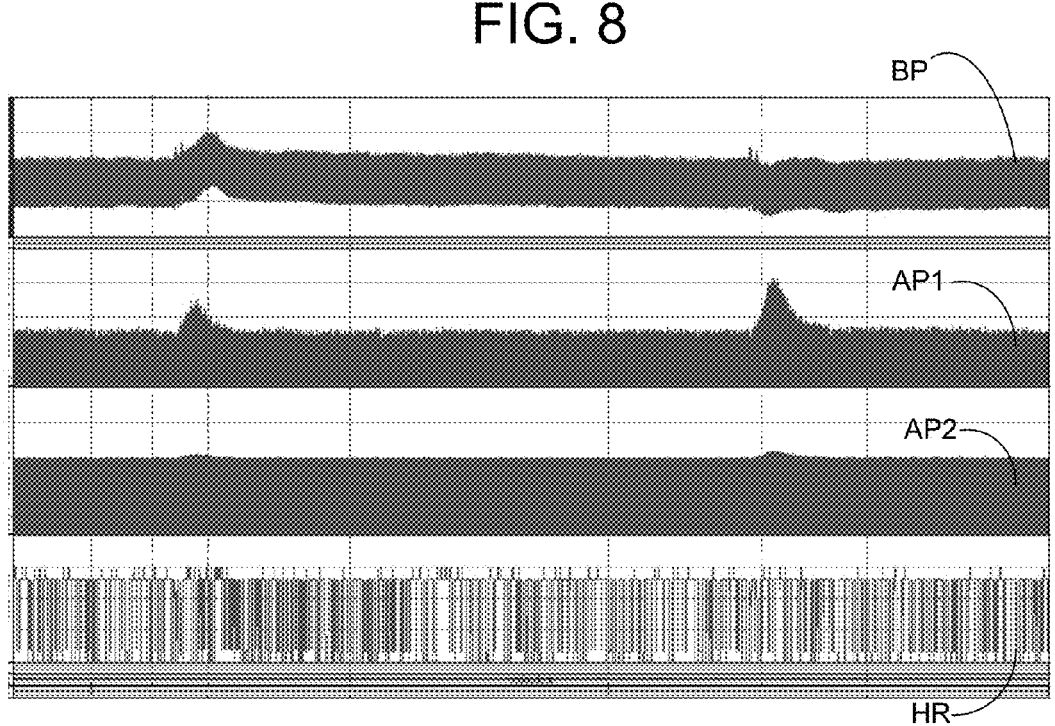

FIG. 8 graphically illustrates further exemplary experimental data on guinea pig #5. The graphs of FIG. 8 show repeatability of the effect seen in the previous graph. The animal, histamine and signal are the same as the graphs in FIG. 7.

It is significant that the effects shown above were repeated several times with this animal (guinea pig #5), without any loss of nerve activity observed. We could move the electrodes proximally and distally along the vagus nerve and achieve the same effect. It was, therefore, concluded that the effect was being achieved without damaging the nerve.

Figure 9:
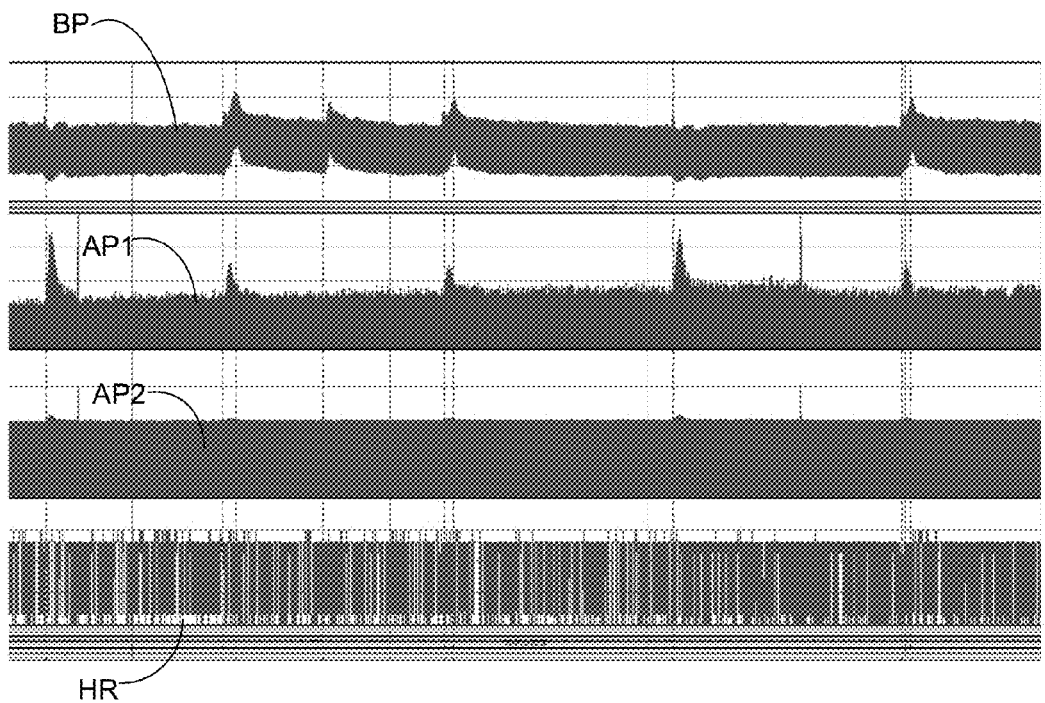

FIG. 9 graphically illustrates subsequent exemplary experimental data on guinea pig #5. The graphs of FIG. 9 show the effect of a 25 Hz, 100 μS, 1V square wave that switches polarity from + to − voltage every second. This signal is applied to both left and right vagus nerve in guinea pig #5 when injected with 8 μg/kg histamine to cause airway pressure to increase. From left to right, the vertical dotted lines coincide with airway pressure events associated with: (1) histamine alone (large airway spike—followed by a very brief manual occlusion of the airway tube); (2) histamine with a 200 μS signal applied (smaller airway spike); (3) a 100 μS electrical signal alone (no airway spike); (4) histamine with a 100 μS signal applied (smaller airway spike again); (5) histamine alone (large airway spike); and (6) histamine with the 100 μS signal applied.

This evidence strongly suggests that the increase in airway pressure due to histamine can be significantly reduced by the application of a 25 Hz, 100 μS, 1V square wave with alternating polarity on the vagus nerve.

Figure 10:
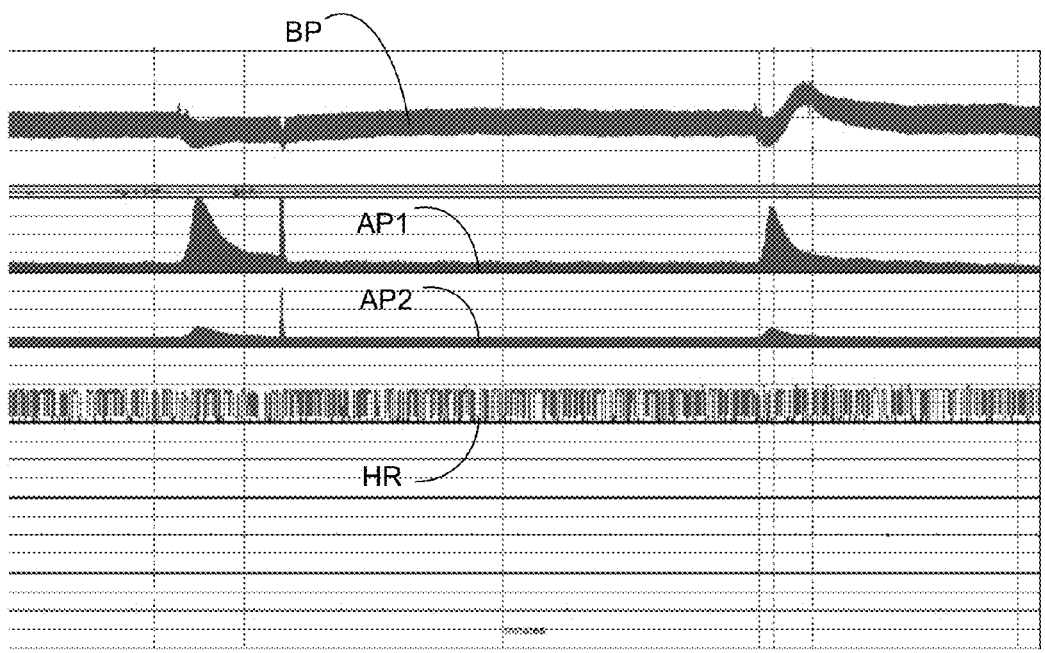

FIG. 10 graphically illustrates exemplary experimental data on guinea pig #6. The graphs in FIG. 10 show the effect of a 25 Hz, 200 μS, 1V square wave that switches polarity from + to − voltage every second. This signal is applied to both left and right vagus nerve in guinea pig #6 when injected with 16 μg/kg histamine to cause airway pressure to increase. (Note that this animal demonstrated a very high tolerance to the effects of histamine, and therefore was not an ideal test subject for the airway constriction effects, however, the animal did provide us with the opportunity to test modification of other signal parameters.)

In this case, the first peak in airway pressure is from histamine alone, the next peak is histamine with the signal applied. It is clearly shown that the increase in airway pressure due to histamine is reduced moderately in its peak, and most definitely in its duration, when in the presence of the 25 Hz, 200 μS, 1V square wave with alternating polarity on the vagus nerve.

Figure 11:
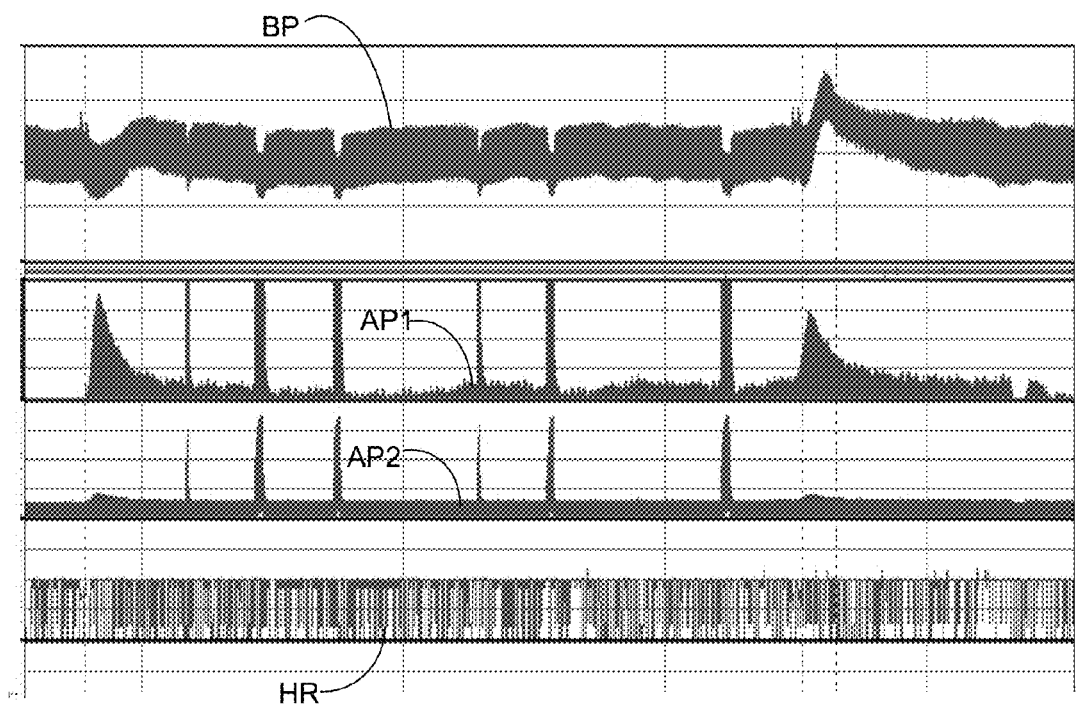

FIG. 11 graphically illustrates additional exemplary experimental data on guinea pig #6. As mentioned above, guinea pig #6 in the graphs of FIG. 10 above needed more histamine than other guinea pigs (16-20 μg/kg vs 8 μg/kg) to achieve the desired increase in airway pressure. Also, the beneficial effects of the 1V signal were less pronounced in pig #6 than in #5. Consequently, we tried increasing the voltage to 1.5V. The first airway peak is from histamine alone (followed by a series of manual occlusions of the airway tube), and the second peak is the result of histamine with the 1.5V, 25 Hz, 200 μS alternating polarity signal. The beneficial effects are seen with slightly more impact, but not substantially better than the 1V.

Figure 12:
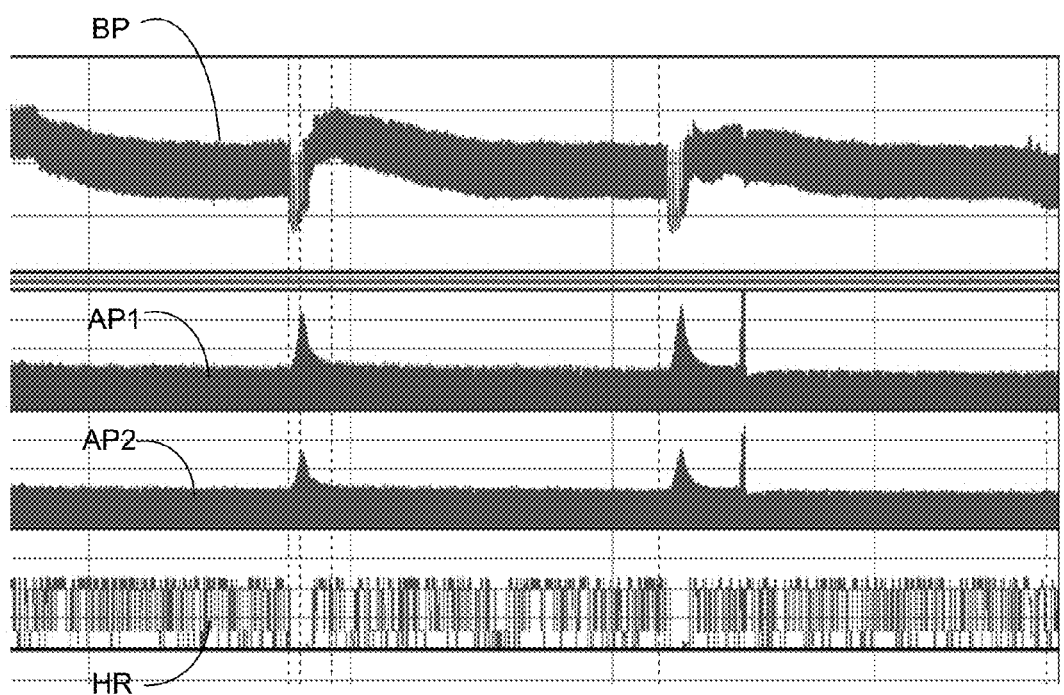

FIG. 12 graphically illustrates further exemplary experimental data on guinea pig #6. Since guinea pig #6 was losing its airway reaction to histamine, we tried to determine if the 25 Hz, 200 μS, 1V, alternating polarity signal could mitigate the effects of a 20V, 20 Hz airway pressure stimulating signal that has produced a simulated asthmatic response. The first airway peak is the 20V, 20 Hz stimulator signal applied to increase pressure, then switched over to the 25 Hz, 200 μS, 1V, alternating polarity signal. The second peak is the 20V, 20 Hz signal alone. The first peak looks modestly lower and narrower than the second. The 25 Hz, 200 μS, 1V signal may have some beneficial airway pressure reduction after electrical stimulation of airway constriction.

Figure 13:
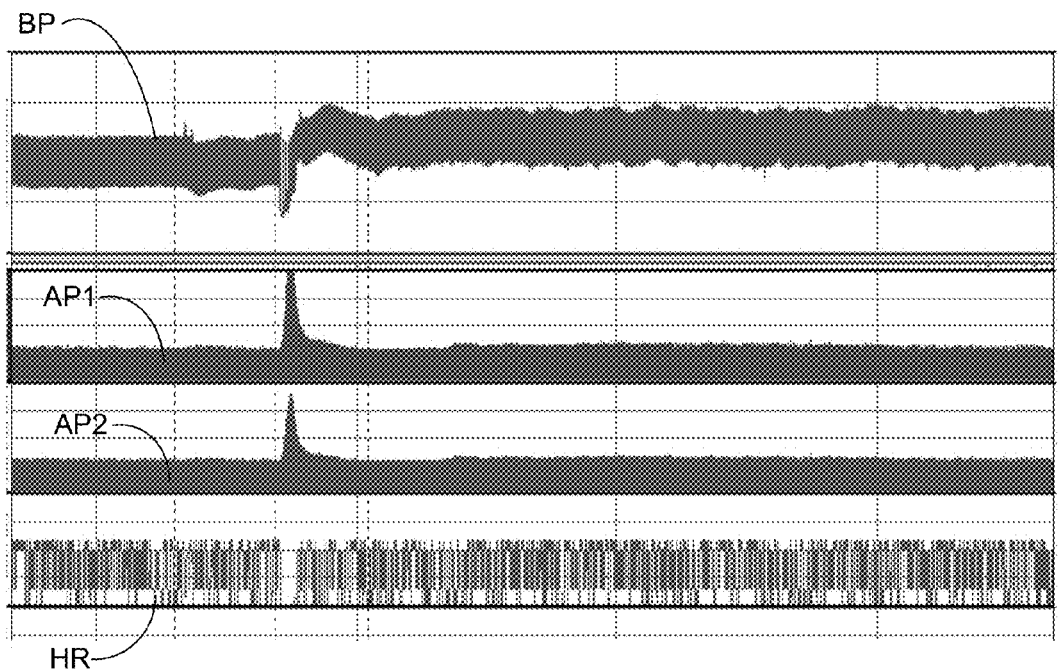

FIG. 13 graphically illustrates subsequent exemplary experimental data. On guinea pig #6 we also investigated the effect of the 1V, 25 Hz, and 200 μS alternating polarity signal. Even after application of the signal for 10 minutes continuously, there was no loss of nerve conduction or signs of damage.

Figure 14:
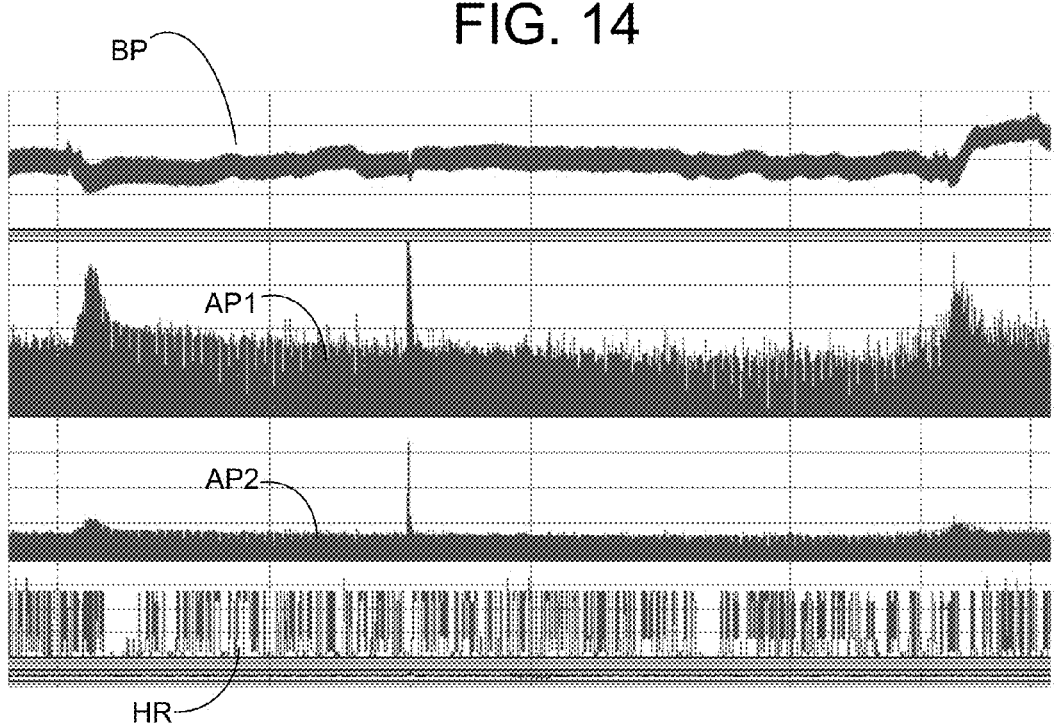
Figure 15:
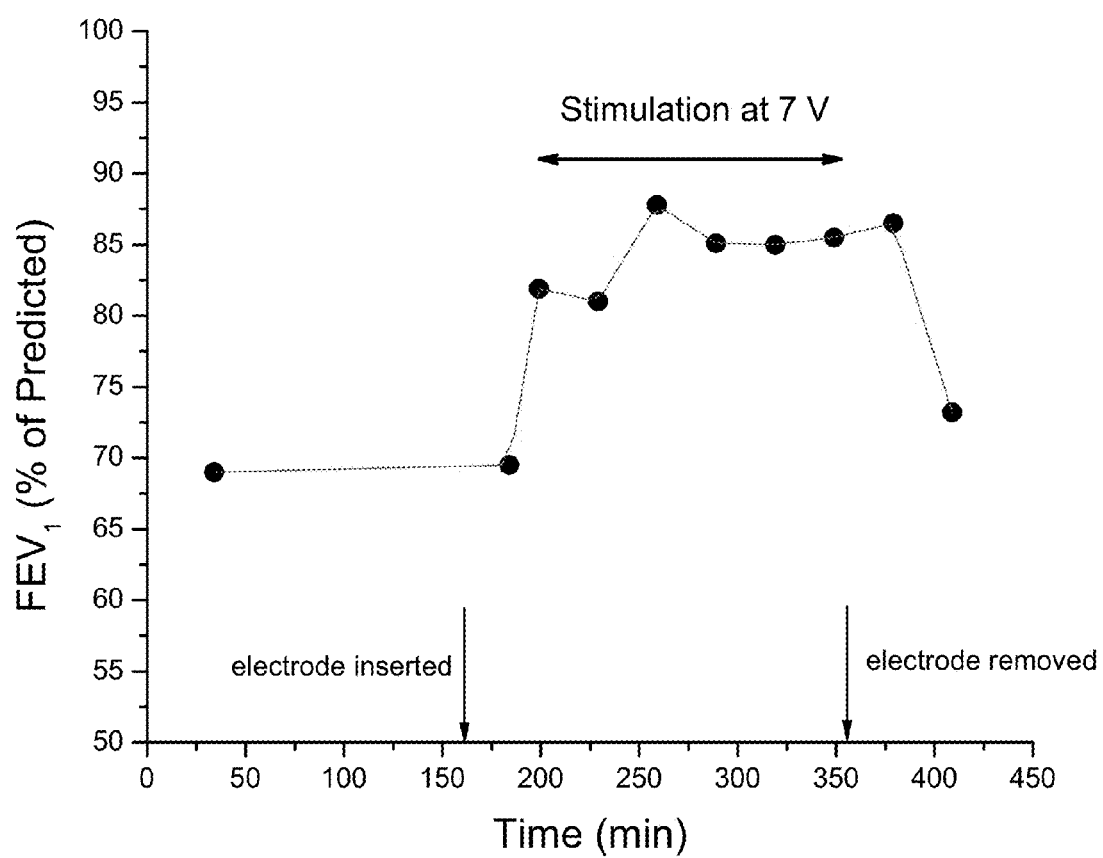
Figure 16:
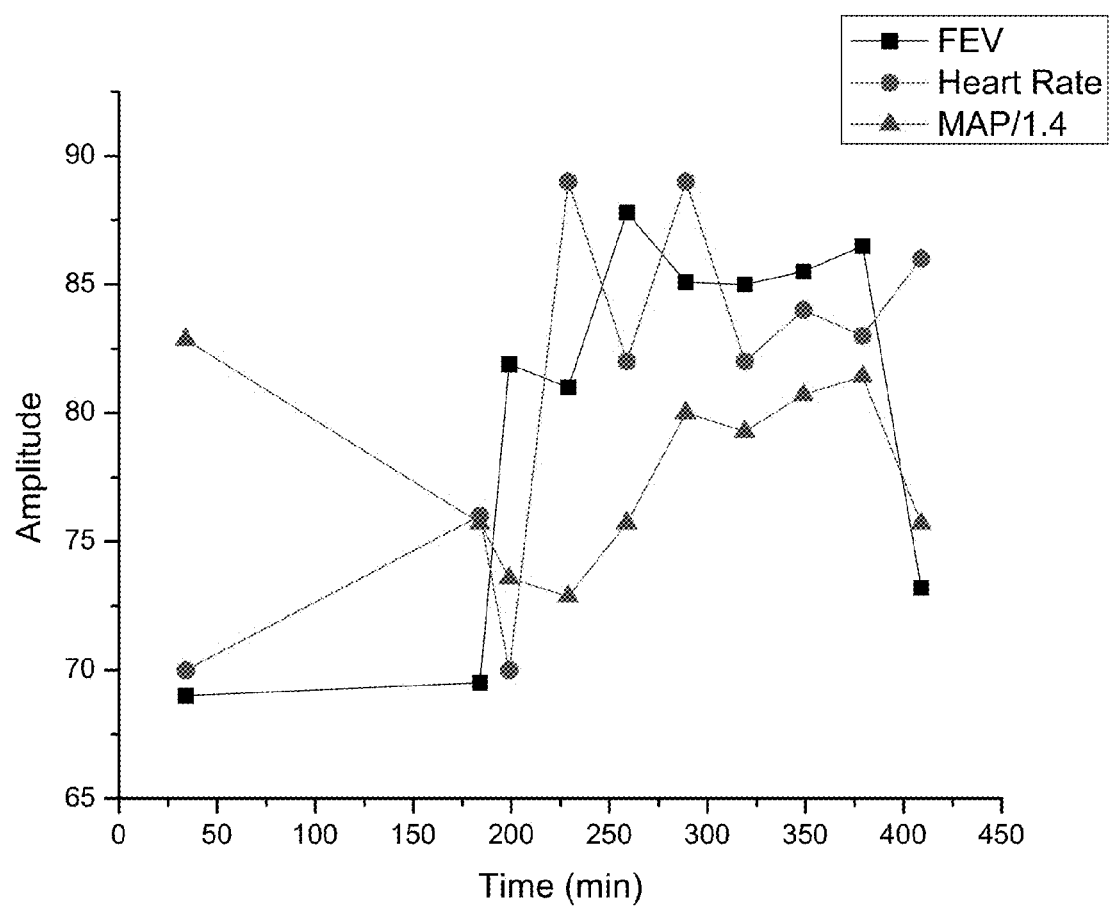

FIG. 14 graphically illustrates exemplary experimental data on guinea pig #8. The graph below shows the effect of a 25 Hz, 200 μS, 1V square wave that switches polarity from + to − voltage every second. This signal is applied to both left and right vagus nerve in guinea pig #8 when injected with 12 μg/kg histamine to cause airway pressure to increase. The first peak in airway pressure is from histamine alone, the next peak is histamine with the signal applied. It is clearly shown that the increase in airway pressure due to histamine is reduced in the presence of the 25 Hz, 200 μS, 1V square wave with alternating polarity on the vagus nerve. We have reproduced this effect multiple times, on 4 different guinea pigs, on 4 different days.

The airway constriction induced by histamine in guinea pigs can be significantly reduced by applying appropriate electrical signals to the vagus nerve.

We found at least 2 separate frequency ranges that have this effect. At 1000 Hz, 6V, 400 μS the constriction is reduced, but there is evidence that this is too much power for the nerve to handle. This may be mitigated by different electrode lead design in future tests. Different types of animals also may tolerate differently differing power levels.

With a 25 Hz, 1V, 100-200 μS signal applied to the vagus nerve, airway constriction due to histamine is significantly reduced. This has been repeated on multiple animals many times. There is no evidence of nerve damage, and the power requirement of the generator is reduced by a factor of between 480 (40×6×2) and 960 (40×6×4) versus the 1000 Hz, 6V, 400 μS signal.

In addition to the exemplary testing described above, further testing on guinea pigs was made by applicant to determine the optimal frequency range for reducing bronchoconstriction. These tests were all completed similarly as above by first establishing a consistent response to i.v. histamine, and then performing nerve stimulation at variations of frequency, voltage and pulse duration to identity parameters that attenuate responses to i.v. histamine. The tests were conducted on over 100 animals at the following frequency values: 1 Hz, 10 Hz, 15 Hz, 25 Hz, 50 Hz, 250 Hz, 500 Hz, 1000 Hz, 2000 Hz and 3000 Hz at pulse durations from 0.16 ms to 0.4 ms with most of the testing done at 0.2 ms. In each of the tests, applicant attempted to achieve a decrease in the histamine transient. Any decrease was noted, while a 50% reduction in histamine transient was considered a significant decrease.

The 25 Hz signal produced the best results by far with about 68% of the animals tested (over 50 animals tested at this frequency) achieving a reduction in histamine transient and about 17% of the animals achieving a significant (i.e., greater than 50%) reduction. In fact, 25 Hz was the only frequency in which any animal achieved a significant decrease in the histamine transient. About 30% of the animals produced no effect and only 2% (one animal) resulted in an increase in the histamine transient.

The 15 Hz signal was tested on 18 animals and showed some positive effects, although not as strong as the 25 Hz signal. Seven of the animals (39%) demonstrated a small decrease in histamine transient and none of the animals demonstrated an increase in histamine transient. Also, none of the animals achieved a significant (greater than 50%) reduction as was seen with the 25 Hz signal.

Frequency ranges below 15 Hz had little to no effect on the histamine transient, except that a 1 Hz signal had the opposite effect on one animal (histamine transient actually increased indicating a further constriction of the bronchial passages). Frequency ranges at or above 50 Hz appeared to either have no effect or they increased the histamine transient and thus increased the bronchoconstriction.

These tests demonstrate that applicant has made the surprising and unexpected discovery that a signal within a small frequency band will have a clinically significant impact on reducing the magnitude of bronchial constriction on animals subject to histamine. In particular, applicant has shown that a frequency range of about 15 Hz to about 50 Hz will have some positive effect on counteracting the impact of histamine, thereby producing bronchodilation. Frequencies outside of this range do not appear to have any impact and, in some case, make the bronchoconstriction worse. In particular, applicant has found that the frequency signal of 25 Hz appears to be the optimal and thus preferred frequency as this was the only frequency tested that resulted in a significant decrease in histamine transient in at least some of the animals and the only frequency tested that resulted in a positive response (i.e., decrease in histamine transient) in at least 66% of the treated animals.

FIGS. 15-18 graphically illustrate exemplary experimental data obtained on five human patients in accordance with multiple embodiments of the present invention. In the first patient (see FIGS. 15 and 16), a 34 year-old, Hispanic male patient with a four year history of severe asthma was admitted to the emergency department with an acute asthma attack. He reported self treatment with albuterol without success. Upon admission, the patient was alert and calm but demonstrated bilateral wheezing, elevated blood pressure (BP) (163/92 mmHg) related to chronic hypertension, acute bronchitis, and mild throat hyperemia. All other vital signs were normal. The patient was administered albuterol (2.5 mg), prednisone (60 mg PO), and zithromax (500 mg PO) without improvement. The spirometry assessment of the lung function revealed a Forced Expiratory Volume in 1 second ($FEV_1$) of 2.68 l/min or 69% of predicted. Additional albuterol was administered without benefit and the patient was placed on supplemental oxygen (2 l/min).

A study entailing a new investigational medical device for stimulating the selected nerves near the carotid sheath was discussed with the patient and, after review, the patient completed the Informed Consent. Following a 90 minute observational period without notable improvement in symptoms, the patient underwent placement of a percutaneous, bipolar electrode to stimulate the selected nerves (see FIG. 16). Using anatomical landmarks and ultrasound guidance, the electrode was inserted to a position near the carotid sheath, and parallel to the vagus nerve.

The electrode insertion was uneventful and a sub-threshold test confirmed the device was functioning. Spirometry was repeated and $FEV_1$ remained unchanged at 2.68 l/min. Stimulation (25 Hz, 300 us pulse width signal) strength was gradually increased until the patient felt a mild muscle twitch at 7.5 volts then reduced to 7 volts. This setting achieved therapeutic levels without discomfort and the patient was able to repeat the $FEV_1$ test without difficulty. During stimulation, the $FEV_1$ improved immediately to 3.18 l/min and stabilized at 3.29 l/min (85% predicted) during 180 minutes of testing. The benefit remained during the first thirty minutes after terminating treatment, then decreased. By 60 minutes post stimulation, dyspnea returned and $FEV_1$ decreased to near pre-stimulation levels (73% predicted) (FIG. 2). The patient remained under observation overnight to monitor his hypertension and then discharged. At the 1-week follow-up visit, the exam showed complete healing of the insertion site, and the patient reported no after effects from the treatment.

This was, to the inventor's knowledge, the first use of nerve stimulation in a human asthma patient to treat bronchoconstriction. In the treatment report here, invasive surgery was not required. Instead a minimally invasive, percutaneous approach was used to position an electrode in close proximity to the selected nerves. This was a relatively simple and rapid procedure that was performed in the emergency department and completed in approximately 10 minutes without evidence of bleeding or scarring.

Figure 17:
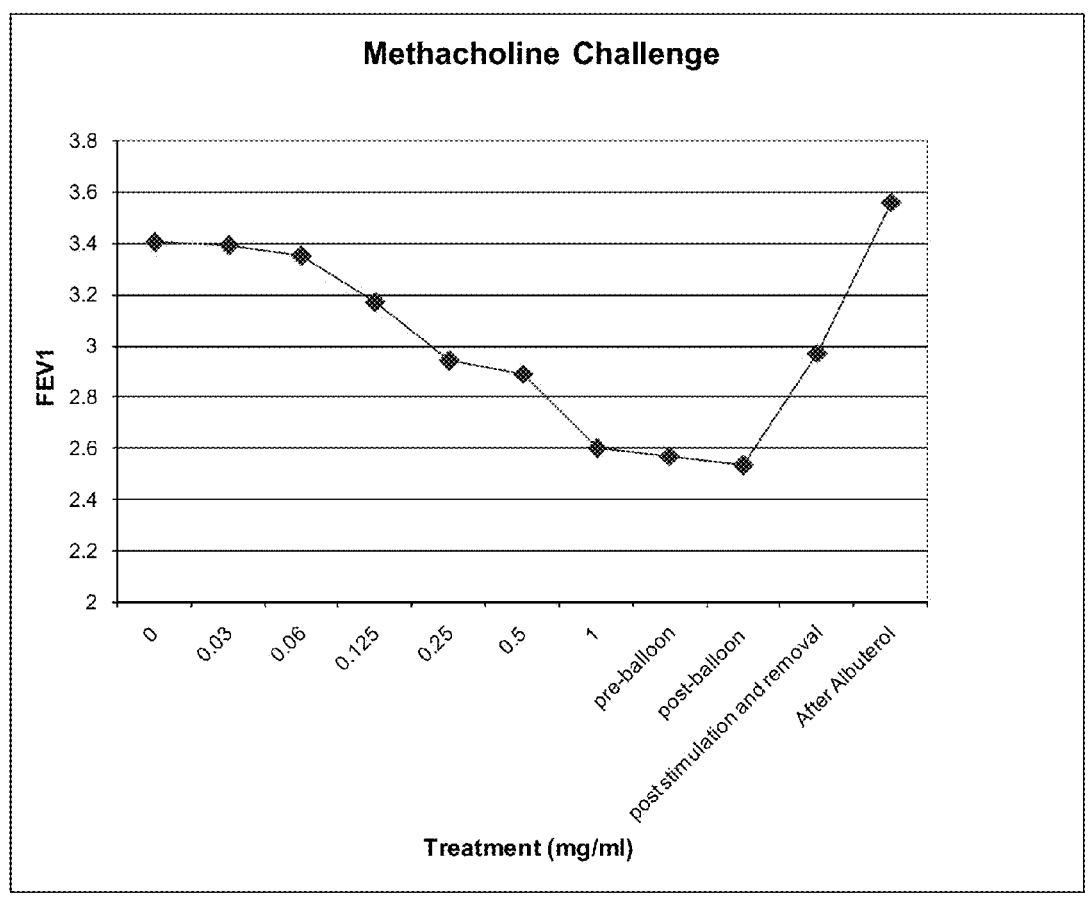

FIG. 17 graphically illustrates another patient treated according to the present invention. Increasing doses of methacholine were given until a drop of 24% in $FEV_1$ was observed at 1 mg/ml. A second $FEV_1$ was taken prior to insertion of the electrode. The electrode was then inserted and another $FEV_1$ taken after electrode insertion and before stimulation. The stimulator was then turned on to 10 V for 4 minutes, the electrode removed and a post-stimulation $FEV_1$ taken showing a 16% increase. A final rescue albuterol treatment restored normal $FEV_1$.

FIG. 18 is a table summarizing the results of all five human patients. In all cases, $FEV_1$ values were measured prior to administration of the electrical impulse delivery to the patient according to the present invention. In addition, $FEV_1$ values were measures at every 15 minutes after the start of treatment. A 12% increase in $FEV_1$ is considered clinically significant. All five patients achieved a clinically significant increase in $FEV_1$ of 12% or greater in 90 minutes or less, which represents a clinically significant increase in an acute period of time. In addition, all five patients achieved at least a 19% increase in $FEV_1$ in 150 minutes or less.

As shown, the first patient initially presented with an $FEV_1$ of 61% of predicted. Upon application of the electrical impulse described above, the first patient achieved at least a 12% increase in $FEV_1$ in 15 minutes or less and achieved a peak increase in $FEV_1$ of 43.9% after 75 minutes. The second patient presented with an $FEV_1$ of 51% of predicted, achieved at least a 12% increase in $FEV_1$ in 30 minutes or less and achieved a peak increase in $FEV_1$ of 41.2% after 150 minutes. The third patient presented with an $FEV_1$ of 16% of predicted, achieved at least a 12% increase in $FEV_1$ in 15 minutes or less and achieved a peak increase in $FEV_1$ of about 131.3% in about 150 minutes. However, it should be noted that this patient's values were abnormal throughout the testing period. The patient was not under extreme duress as a value of 16% of predicted would indicate. Therefore, the exact numbers for this patient are suspect, although the patient's symptoms clearly improved and the $FEV_1$ increased in any event. The fourth patient presented with an $FEV_1$ of predicted of 66%, achieved at least a 12% increase in $FEV_1$ in 90 minutes or less and achieved a peak increase in $FEV_1$ of about 19.7% in 90 minutes or less. Similarly, the fifth patient presented with an $FEV_1$ of predicted of 52% and achieved a 19.2% peak increase in $FEV_1$ in 15 minutes or less. The electrode in the fifth patient was unintentionally removed around 30 minutes after treatment and, therefore, a true peak increase in $FEV_1$ was not determined.

In U.S. patent application Ser. No. 10/990,938 filed Nov. 17, 2004 (Publication Number US2005/0125044A1), Kevin J. Tracey proposes a method of treating many diseases including, among others, asthma, anaphylactic shock, sepsis and septic shock by electrical stimulation of the vagus nerve. However, the examples in the Tracey application use an electrical signal that is 1 to 5V, 1 Hz and 2 mS to treat endotoxic shock, and no examples are shown that test the proposed method on an asthma model, an anaphylactic shock model, or a sepsis model. The applicants of the present application performed additional testing to determine if Tracey's proposed method has any beneficial effect on asthma or blood pressure in the model that shows efficacy with the method used in the present application. The applicants of the present application sought to determine whether Tracey's signals can be applied to the vagus nerve to attenuate histamine-induced bronchoconstriction and increase in blood pressure in guinea pigs.

Male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 1 to 5 volts, 1 Hz, 2 mS to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP (red) shows blood pressure, second line AP1 shows airway pressure, third line AP2 shows airway pressure on another sensor, the last line HR is the heart rate derived from the pulses in the blood pressure.

Figure 19:
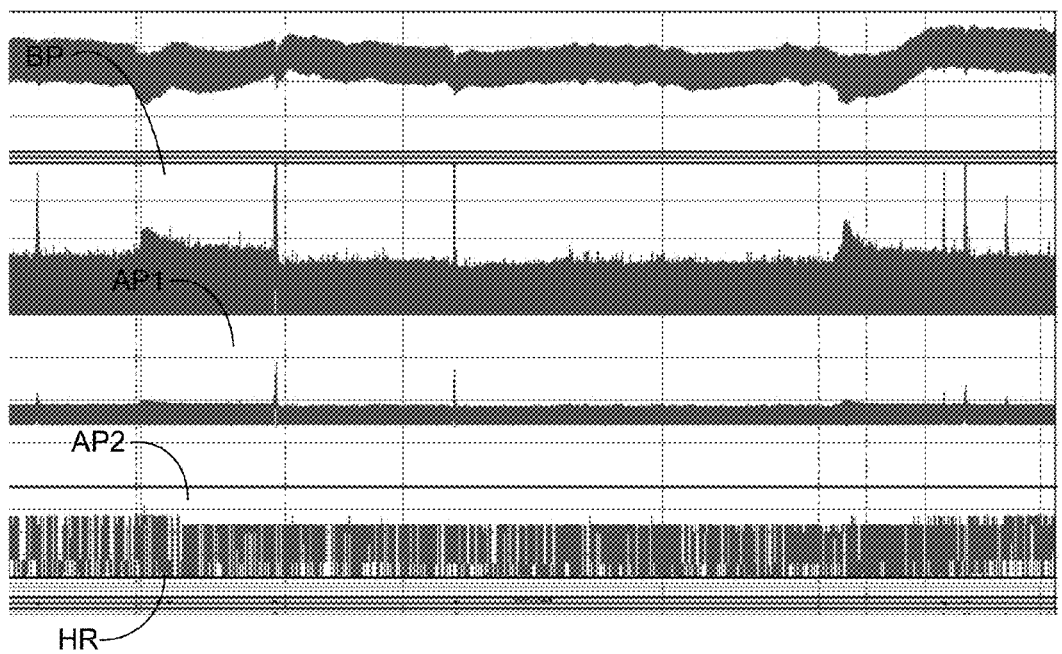
FIGS. 19-24 graphically illustrate the inability of signals taught by U.S. patent application Ser. No. 10/990,938 to achieve the results of the present invention.

FIG. 19 graphically illustrates exemplary experimental data from a first experiment on another guinea pig. The graph shows the effects of Tracey's 1V, 1 Hz, 2 mS waveform applied to both vagus nerves on the guinea pig. The first peak in airway pressure is from histamine alone, after which Tracey's signal was applied for 10 minutes as proposed in Tracey's patent application. As seen from the second airway peak, the signal has no noticeable effect on airway pressure. The animal's vital signs actually stabilized, seen in the rise in blood pressure, after the signal was turned off.

Figure 20:
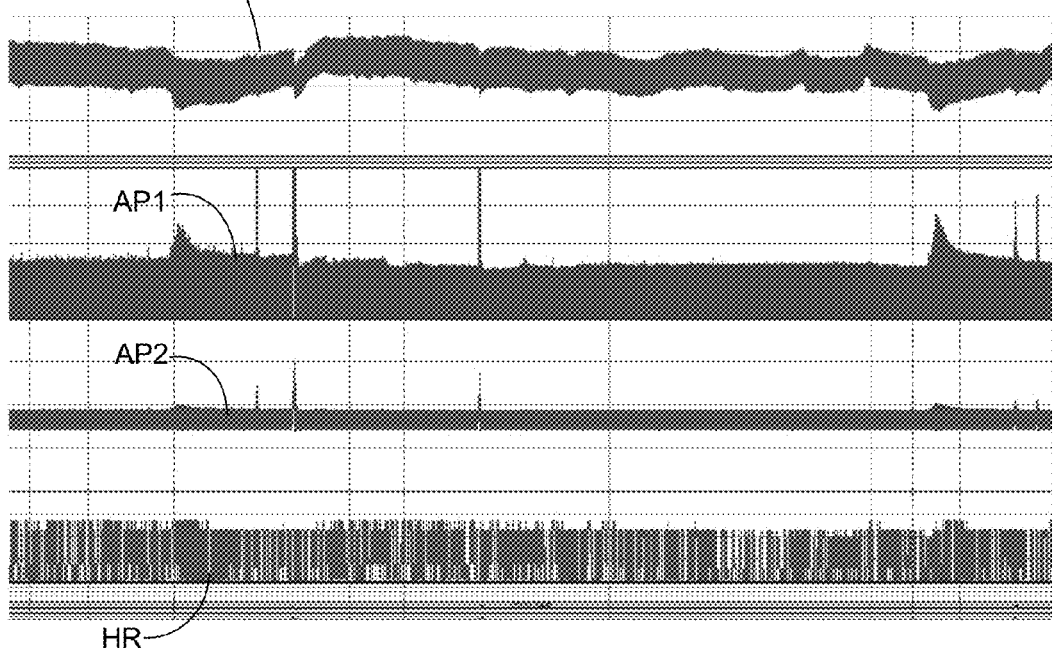

FIG. 20 graphically illustrates exemplary experimental data from a second experiment on the guinea pig in FIG. 19. The graph shows the effects of Tracey's 1V, 1 Hz, 2 mS waveform with the polarity reversed (Tracey did not specify polarity in the patent application) applied to both vagus nerves on the guinea pig. Again, the signal has no beneficial effect on airway pressure. In fact, the second airway peak from the signal and histamine combination is actually higher than the first peak of histamine alone.

Figure 21:
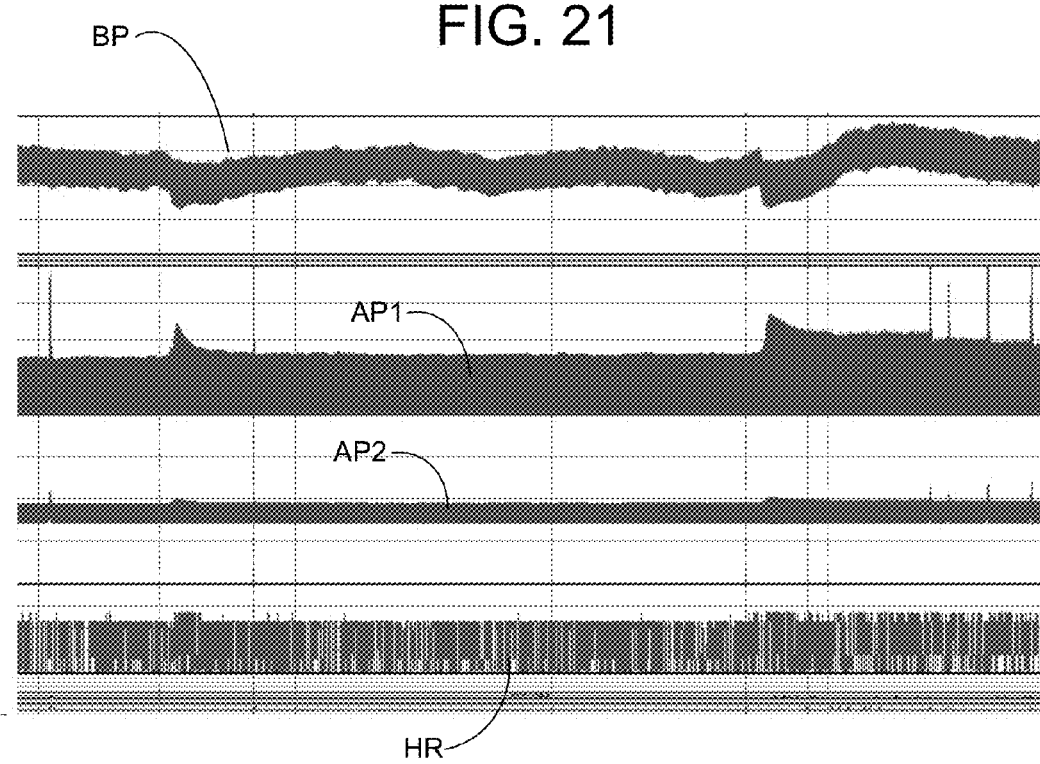

FIG. 21 graphically illustrates exemplary experimental data from a third experiment on the guinea pig in FIG. 19. The graph shows the effects of Tracey's 1V, 1 Hz, 2 mS waveform applied to both vagus nerves on the guinea pig. Again, the signal has no beneficial effect on airway pressure. Instead, it increases airway pressure slightly throughout the duration of the signal application.

Figure 22:
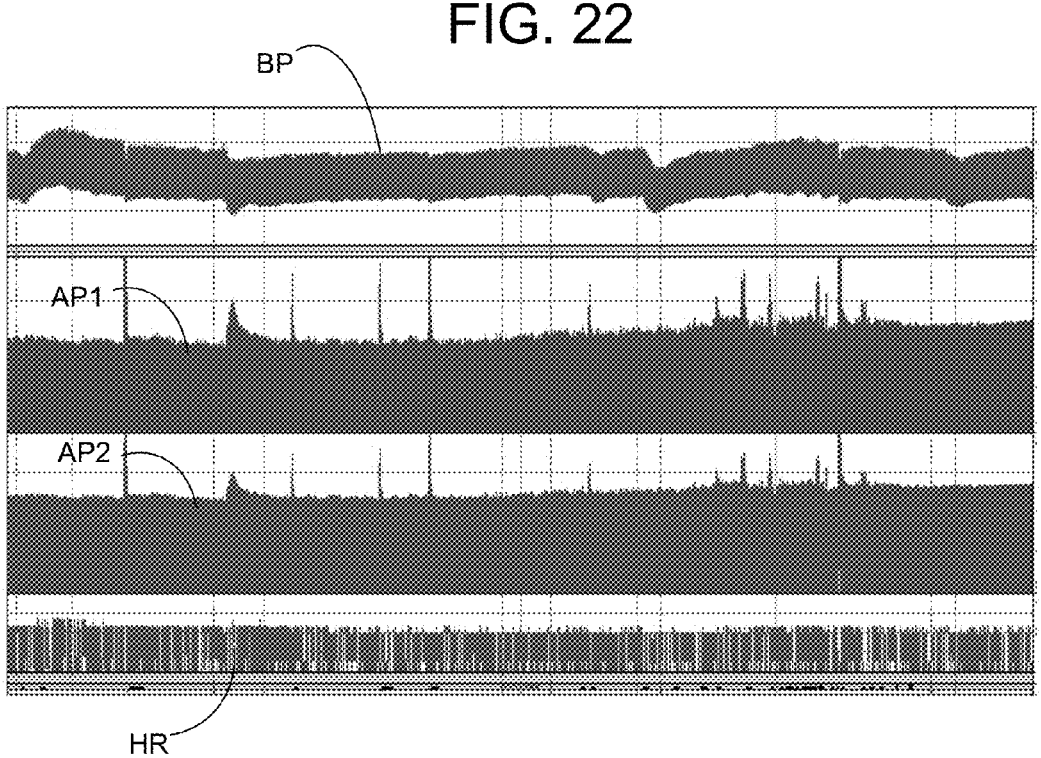

FIG. 22 graphically illustrates additional exemplary experimental data from an experiment on a subsequent guinea pig. The graph shows, from left to right, application of the 1.2V, 25 Hz, 0.2 mS signal disclosed in the present application, resulting in a slight decrease in airway pressure in the absence of additional histamine. The subsequent three electrical stimulation treatments are 1V, 5V, and 2.5V variations of Tracey's proposed signal, applied after the effects of a histamine application largely had subsided. It is clear that the Tracey signals do not cause a decrease in airway pressure, but rather a slight increase, which remained and progressed over time.

Figure 23:
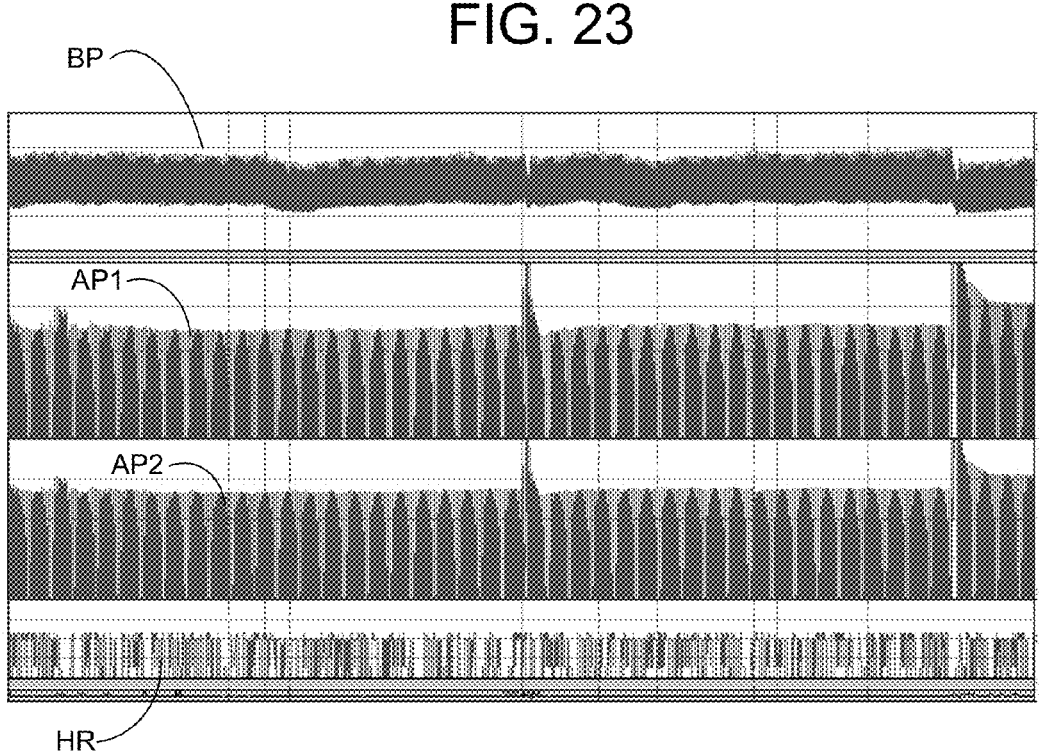

FIG. 23 graphically illustrates further exemplary experimental data from additional experiments using signals within the range of Tracey's proposed examples. None of the signals proposed by Tracey had any beneficial effect on airway pressure. Factoring in a potential range of signals, one experiment used 0.75V, which is below Tracey's proposed range, but there was still no beneficial effect on airway pressure.

Figure 24:
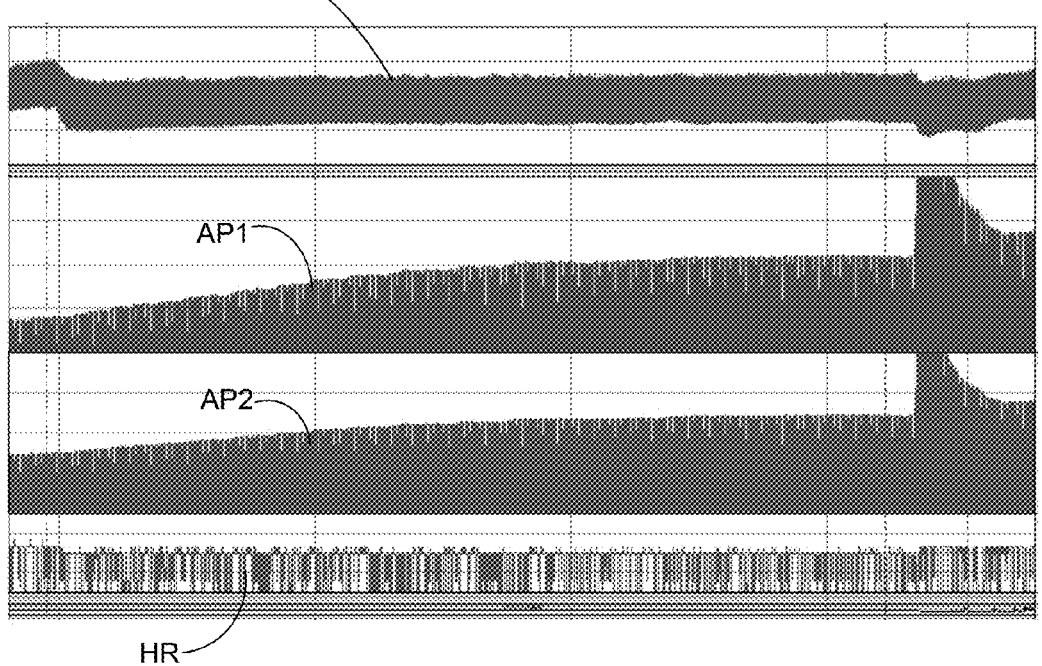

FIG. 24 graphically illustrates exemplary experimental data from subsequent experiments showing the effect of Tracey's 5V, 1 Hz, 2 mS signal, first without and then with additional histamine. It is clear that the airway pressure increase is even greater with the signal, as the airway pressure progressively increased during the course of signal application. Adding the histamine after prolonged application of the Tracey signal resulted in an even greater increase in airway pressure.

The full range of the signal proposed by Tracey in his patent application was tested in the animal model of the present application. No reduction in airway pressure was seen. Most of the voltages resulted in detrimental increases in airway pressure and detrimental effects to vital signs, such as decreases in blood pressure.

In International Patent Application Publication Number WO 93/01862, filed Jul. 22, 1992, Joachim Wernicke and Reese Terry (hereinafter referred to as "Wernicke") propose a method of treating respiratory disorders such as asthma, cystic fibrosis and apnea by applying electric signals to the patient's vagus nerve. However, Wernicke specifically teaches to apply a signal that blocks efferent activity in the vagus nerve to decrease the activity of the vagus nerve to treat asthma. Moreover, the example disclosed in Wernicke for the treatment of asthma is an electrical impulse having a frequency of 100 Hz, a pulse width of 0.5 ms, an output current of 1.5 mA and an OFF time of 10 seconds for every 500 seconds of ON time (see Table 1 on page 17 of Wernicke). The applicants of the present application performed additional testing to determine if Wernicke's proposed method has any beneficial effect on bronchodilation or blood pressure in the model that shows efficacy with the method used in the present application. The applicants of the present application sought to determine whether Wernicke's signal can be applied to the vagus nerve to attenuate histamine-induced bronchoconstriction and increase in blood pressure in guinea pigs.

Similar to the Tracey testing, male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 100 Hz, 0.5 ms and 1.5 mA output current to identify parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP (red) shows blood pressure, second line AP1 shows airway pressure, third line AP2 shows airway pressure on another sensor, the last line HR is the heart rate derived from the pulses in the blood pressure.

Figure 25:
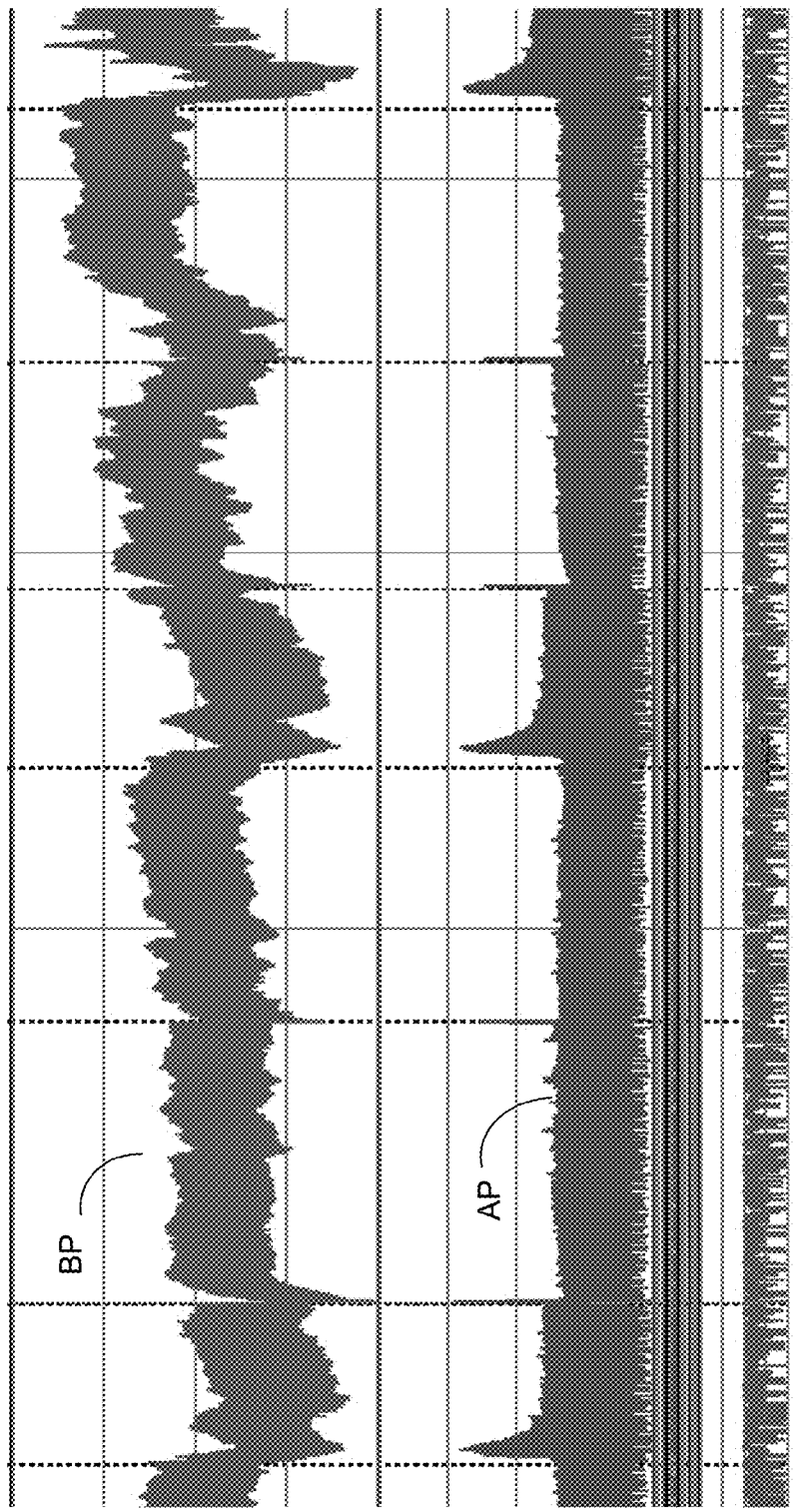
FIGS. 25 and 26 graphically illustrate the inability of signals taught by International Patent Application Publication Number WO 93/01862 to achieve the results of the prevent invention.
Figure 26:
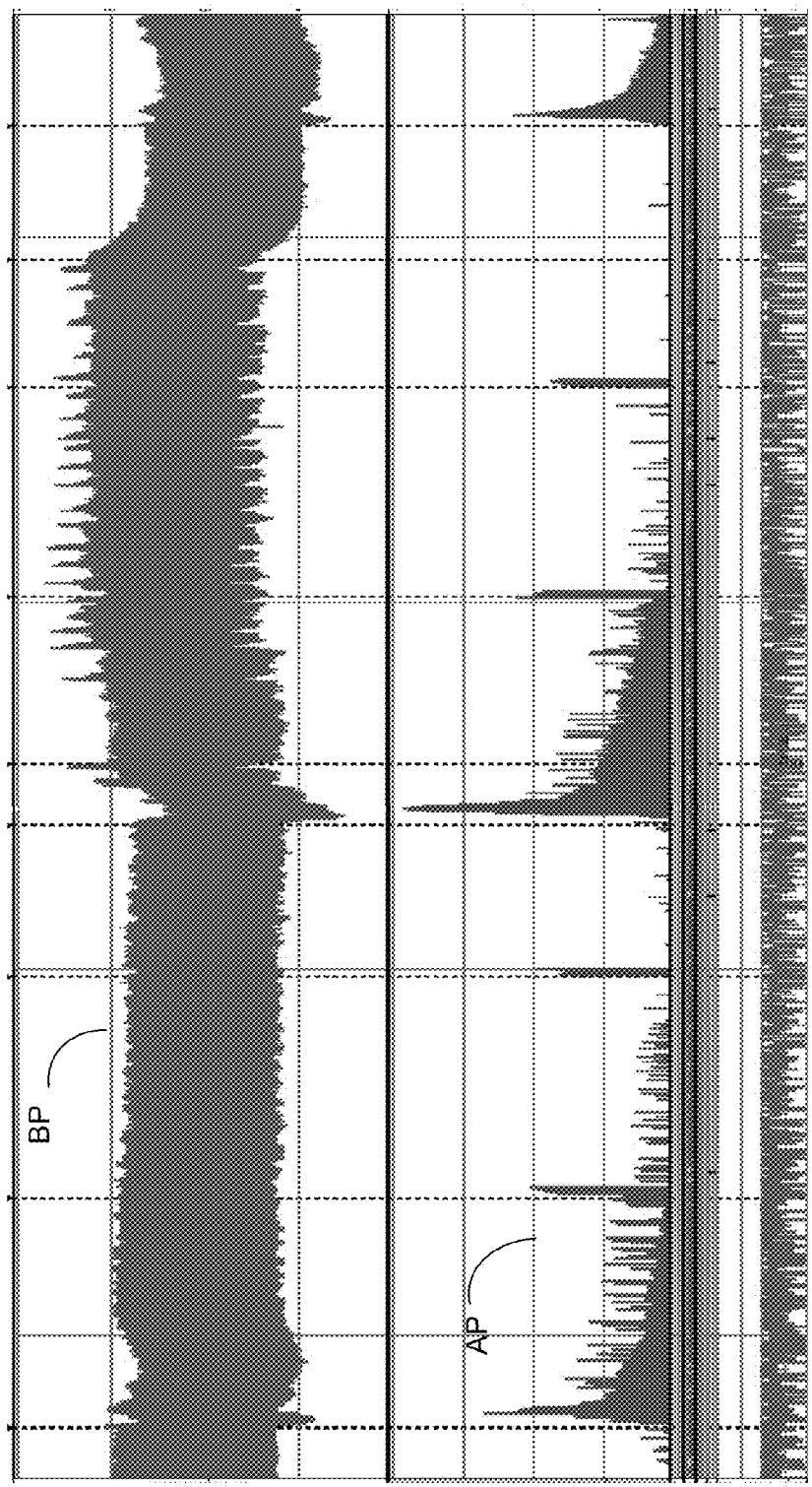

FIGS. 25 and 26 graphically illustrate exemplary experimental data from the experiment on another guinea pig. The graph shows the effects of Wernicke's 100 Hz, 1.5 mA, 0.5 mS waveform applied to both vagus nerves on the guinea pig. FIG. 25 illustrates two peaks in airway pressure (AP) from histamine alone with no treatment (the first two peaks) and a third peak at the right of the graph after which Wernicke's signal was applied at 1.2 mA. As shown, the results show no beneficial result on the histamine-induced airway pressure increase or the blood pressure at 1.2 mA. In FIG. 26, the first and third peaks in airway pressure (AP) are from histamine along with no treatment and the second peak illustrates airway pressure after Wernicke's signal was applied at 1.8 mA. As shown, the signal actually increased the histamine-induced airway pressure at 2.8 mA, making it clinically worse. Thus, it is clear the Wernicke signals do not cause a decrease in airway pressure.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a medical disorder in a patient, the method comprising:
  advancing an introducer through an incision in an outer skin surface of a neck of a patient to a target site at or near a vagus nerve of a patient;
  introducing one or more electrodes through the introducer to the target site;
  positioning the one or more electrodes adjacent the vagus nerve exterior to a carotid sheath of the vagus nerve;
  generating an electrical impulse from a location exterior to the patient; and
  transmitting the electrical impulse through the incision in the outer skin surface of the neck of the patient to the one or more electrodes such that the electrical impulse is applied to the vagus nerve, wherein the electrical impulse is sufficient to modulate the vagus nerve to treat the medical disorder, wherein the medical disorder is bronchoconstriction and the electrical impulse is sufficient to increase a forced expiratory volume in 1 second of the patient by a clinically significant amount in a period of time less than 6 hours.

2. The method of claim 1, wherein the electrical impulse has a frequency from 15 Hz to 50 Hz.

3. The method of claim 1, wherein the electrical impulse is insufficient to simulate efferent fibers of the vagus nerve.

4. The method of claim 1, wherein the electrical impulse is of an amplitude from 1 volt to 12 volts.

5. The method of claim 1, wherein the electrical impulse has a pulsed on-time from 50 microseconds to 500 microseconds.

6. The method of claim 1, wherein the electrical impulse has a pulsed on-time from 200 microseconds to 400 microseconds and an amplitude from 6 volts to 12 volts.

7. The method of claim 1, wherein the electrical impulse is sufficient to treat the medical disorder in the patient in less than 2 hours.

8. The method of claim 1, wherein the electrical impulse is sufficient to treat the medical disorder in the patient in less than 1 hour.

9. The method of claim 1, wherein the electrical impulse is sufficient to treat the medical disorder in the patient in less than 15 minutes.

10. The method of claim 1, wherein the electrical impulse has a pulsed on-time from 200 microseconds to 400 microseconds and an amplitude from 6 volts to 12 volts.

11. A device for treating a medical disorder in a patient, the device comprising:
   a source of electrical energy;
   an introducer configured for introduction through an incision in an outer skin surface of a neck of the patient;
   one or more electrodes coupled to the source of electrical energy and configured for advancement through the introducer to a target site at or near a vagus nerve of the patient exterior to a carotid sheath of the vagus nerve; and
   a control unit coupled to the source of electrical energy, wherein the control unit is configured to control the source of electrical energy to generate an electrical impulse and to transmit the electrical impulse through the incision in the outer skin surface of the neck of the patient and the one or more electrodes to the vagus nerve, the electrical impulse being sufficient to modulate the vagus nerve to treat the medical disorder, wherein the medical disorder is bronchoconstriction and the electrical impulse is sufficient to increase a forced expiratory volume in 1 second (FEV1) of the patient by a clinically significant amount in a period of time less than 6 hours.

12. The device of claim 11, wherein the electrical impulse has a frequency from 15 HZ to 50 Hz.

13. The device of claim 11, wherein the electrical impulse is insufficient to simulate efferent fibers of the vagus nerve.

14. The device of claim 11, wherein the electrical impulse is of an amplitude from 1 volt to 12 volts.

15. The device of claim 11, wherein the electrical impulse has a pulsed on-time from 50 microseconds to 500 microseconds.

* * * * *